US012708668B2

(12) United States Patent
Crowley et al.

(10) Patent No.: US 12,708,668 B2
(45) Date of Patent: Aug. 18, 2026

(54) STABLE AQUEOUS ANTI-TFPI ANTIBODY FORMULATION

(71) Applicant: Pfizer Inc., New York, NY (US)

(72) Inventors: Thomas Joseph Crowley, Wilmington, MA (US); Robert Lee Dufield, Overland Park, KS (US); Jennifer Juneau, Sterling, MA (US)

(73) Assignee: Pfizer Inc., New York, NY (US)

( * ) Notice: Subject to any disclaimer, the term of this patent is extended or adjusted under 35 U.S.C. 154(b) by 1062 days.

(21) Appl. No.: 17/755,573

(22) PCT Filed: Nov. 10, 2020

(86) PCT No.: PCT/IB2020/060571

§ 371 (c)(1),
(2) Date: May 2, 2022

(87) PCT Pub. No.: WO2021/094917

PCT Pub. Date: May 20, 2021

(65) Prior Publication Data

US 2023/0035617 A1 Feb. 2, 2023

Related U.S. Application Data

(60) Provisional application No. 63/081,409, filed on Sep. 22, 2020, provisional application No. 62/934,781, filed on Nov. 13, 2019.

(51) Int. Cl.

| | |
|---|---|
| ***A61K 39/395*** | (2006.01) |
| ***A61K 47/12*** | (2006.01) |
| ***A61K 47/22*** | (2006.01) |
| ***A61K 47/26*** | (2006.01) |
| ***A61P 7/04*** | (2006.01) |
| ***C07K 16/38*** | (2006.01) |
| *A61K 39/00* | (2006.01) |

(52) U.S. Cl.

CPC ........ *A61K 39/39591* (2013.01); *A61K 47/12* (2013.01); *A61K 47/22* (2013.01); *A61K 47/26* (2013.01); *A61P 7/04* (2018.01); *C07K 16/38* (2013.01); *A61K 2039/54* (2013.01); *C07K 2317/32* (2013.01); *C07K 2317/565* (2013.01)

(58) Field of Classification Search

None

See application file for complete search history.

(56) References Cited

U.S. PATENT DOCUMENTS

| | | | | |
|---|---|---|---|---|
| 4,816,567 A | 3/1989 | Cabilly et al. | | |
| 5,530,101 A | 6/1996 | Queen et al. | | |
| 5,545,806 A | 8/1996 | Lonberg et al. | | |
| 5,545,807 A | 8/1996 | Surani et al. | | |
| 5,569,825 A | 10/1996 | Lonberg et al. | | |
| 5,585,089 A | 12/1996 | Queen et al. | | |
| 5,625,126 A | 4/1997 | Lonberg et al. | | |
| 5,633,425 A | 5/1997 | Lonberg et al. | | |
| 5,661,016 A | 8/1997 | Lonberg et al. | | |
| 5,693,761 A | 12/1997 | Queen et al. | | |
| 5,693,762 A | 12/1997 | Queen et al. | | |
| 5,750,373 A | 5/1998 | Garrard et al. | | |
| 5,807,715 A | 9/1998 | Morrison et al. | | |
| 5,866,692 A | 2/1999 | Shitara et al. | | |
| 5,997,867 A | 12/1999 | Waldmann et al. | | |
| 6,054,297 A | 4/2000 | Carter et al. | | |
| 6,180,370 B1 | 1/2001 | Queen et al. | | |
| 6,180,377 B1 | 1/2001 | Morgan et al. | | |
| 6,210,671 B1 | 4/2001 | Co et al. | | |
| 6,331,415 B1 | 12/2001 | Cabilly et al. | | |
| 6,350,861 B1 | 2/2002 | Co et al. | | |
| 8,361,469 B2 | 1/2013 | Hilden et al. | | |
| 8,481,030 B2 | 7/2013 | Wang et al. | | |
| 10,550,200 B2 | 2/2020 | Pittman et al. | | |
| 10,875,929 B2 | 12/2020 | Pittman et al. | | |
| 10,894,083 B2 | 1/2021 | Ingram et al. | | |
| 11,634,504 B2 | 4/2023 | Pittman et al. | | |
| 2005/0276823 A1* | 12/2005 | Cini | A61K 47/183 | 424/400 |
| 2006/0088523 A1* | 4/2006 | Andya | A61K 47/26 | 424/133.1 |
| 2009/0238820 A1 | 9/2009 | Allan et al. | | |
| 2011/0268745 A1 | 11/2011 | Hilden et al. | | |
| 2011/0318356 A1 | 12/2011 | Hilden et al. | | |
| 2012/0028901 A1 | 2/2012 | Dockal et al. | | |
| 2012/0108796 A1 | 5/2012 | Wang et al. | | |
| 2012/0269817 A1 | 10/2012 | Wang et al. | | |
| 2013/0136733 A1 | 5/2013 | Parshad et al. | | |
| 2013/0251721 A1 | 9/2013 | Hilden et al. | | |

(Continued)

FOREIGN PATENT DOCUMENTS

| | | |
|---|---|---|
| AU | 2014200227 A1 | 1/2014 |
| EP | 0519596 | 12/1992 |

(Continued)

OTHER PUBLICATIONS

Brown et al. Cancer Res. 47: 3577-3583 1987.
Caceci et al. 1984, Byte 9: 340-362).
Chothia and Lesk, J Mol Biol 196(4): 901-917, 1987.
Chothia et al., 1989, Nature, 342: 877-83.
Daugherty et al., Nucl. Acids Res. 19: 2471-2476, 1991.
International Search Report; PCT/IB2020/060571; 22pages; mailed: Feb. 4, 2021.
Johnson & Wu, 2000, Nucleic Acids Res., 28: 214-8.
Jones et al. Nature 321: 522-525 1986.

(Continued)

*Primary Examiner* — Yunsoo Kim

(57) ABSTRACT

The present invention relates to the field of pharmaceutical formulations of antibodies. Specifically, the present invention relates to a stable liquid antibody formulation and its pharmaceutical preparation and use. This invention is exemplified by an aqueous formulation of an anti-Tissue Factor Pathway Inhibitor (TFPI) antibody.

18 Claims, No Drawings

Specification includes a Sequence Listing.

(56) References Cited

U.S. PATENT DOCUMENTS

| | | | |
|---|---|---|---|
| 2013/0251722 A1 | 9/2013 | Hilden et al. |
| 2014/0065159 A1 | 3/2014 | Ma et al. |
| 2014/0294832 A1 | 10/2014 | Wang et al. |
| 2017/0073428 A1 | 3/2017 | Pittman et al. |
| 2017/0360929 A1 | 12/2017 | Sinha et al. |
| 2018/0000933 A1 | 1/2018 | Ingram et al. |
| 2018/0055940 A1 | 3/2018 | Ma et al. |

FOREIGN PATENT DOCUMENTS

| | | |
|---|---|---|
| EP | 2746294 A2 | 6/2014 |
| EP | 3345615 A1 | 7/2018 |
| RU | 2562114 C2 | 9/2015 |
| WO | 1999058572 | 11/1999 |
| WO | 2001027160 | 4/2001 |
| WO | 2006096491 | 9/2006 |
| WO | 2008/147196 A3 | 2/2009 |
| WO | 2010017196 | 2/2010 |
| WO | 2010032220 | 3/2010 |
| WO | 2010072687 | 7/2010 |
| WO | 2010072691 | 7/2010 |
| WO | 2011104381 | 9/2011 |
| WO | 2011109452 | 9/2011 |
| WO | 2011/147921 A1 | 12/2011 |
| WO | 2012001087 | 1/2012 |
| WO | 2012/135671 A2 | 10/2012 |
| WO | 2013/023251 A1 | 2/2013 |
| WO | 2013/148248 A1 | 10/2013 |
| WO | 2013186719 | 12/2013 |
| WO | 2014/036071 A1 | 3/2014 |
| WO | 2014/144689 A1 | 9/2014 |
| WO | 2014140240 | 9/2014 |
| WO | 2014144577 | 9/2014 |
| WO | 2015007880 | 1/2015 |
| WO | 2016/084912 A1 | 6/2016 |
| WO | 2016120753 | 8/2016 |
| WO | 2016/137108 A1 | 9/2016 |
| WO | 2017029583 | 2/2017 |
| WO | 2017/055966 A1 | 4/2017 |
| WO | 2020075083 | 4/2020 |
| WO | 2021/094917 A1 | 5/2021 |

OTHER PUBLICATIONS

Kohler and Milstein, 1975, Nature 256:495.
Lobuglio et al. Proc. Nat. Acad. Sci. USA 86: 4220-4224, 1989.
MacCallum et al., 1996, J. Mol. Biol., 5:732-45.
Makabe et al., 2008, Journal of Biological Chemistry, 283:1156-1166.
Martin et al., 1989, Proc Natl Acad Sci (USA), 86:9268-9272.
McCafferty et al., 1990, Nature 348:552-554.
Riechmann et al. Nature 332: 323-327, 1988.
Samudrala et al., 1999, Proteins, Structure, Function and Genetics Suppl., 3:194-198.
Shaw et al. J Immunol. 138: 4534-4538, 1987.
Verhoeyen et al. Science 239: 1534-1536, 1988.
Wang, International J. of Pharmaceutics; vol. 185; No. 2; 1999; pp. 129-188.
Wang et al., J. Pharm Sci. 96:1-26, 2007.
Winter et al. Nature 349: 293-299, 1991.
Wong & Lohman, Proc. Natl. Acad. Sci. USA 90: 5428-5432, 1993.
Abumiya, T., et al., "An anti-tissue factor pathway inhibitor (TFPI) monoclonal antibody recognized the third Kunitz domain (K3) of free-form TFPI but not lipoprotein-associated forms in plasma," The Journal of Biochemistry, 1995, 118 (1): 178-182.
Agerso, H., et al., "Pharmacokinetics an anti-TFPI monoclonal antibody (concizumab) blocking the TFPI interaction with the active site of FXa in Cynomolgus monkeys after iv and sc administration," European Journal of Pharmaceutical Science, 2014, 56:65-69.
Anonymous: "Anti-Human TFPI (KUNITZ-2)," XP55313565, Retrieved from the Internet: URL:http://www.sanquin.nl/repository/reagentia/ifu/MW1845.pdf; 2008.
Beringer et al., Remington's Pharmaceutical Sciences, Mack Pub., 21st Edition, 2005, pp. 1072-1076.
Boerner, P., et al., "Production of Antigen-Specific Human Monoclonal Antibodies From In Vitro-Primed Human Splenocytes," The Journal of Immunology, 1991, 147 (1):86-95.
Brovc, E.A., et al., "Protein formulations containing polysorbates: Are metal chelators needed at all?" Antioxidants, 2020, 9(5):441, 13 pp.
Cardinal, M., et al., "A first-in-human study of the safety, tolerability, pharmacokinetics and pharmacodynamics of PF-06741086, an anti-tissue factor pathway inhibitor mAb, in healthy volunteers," Journal of Thrombosis and Haemostasis, 2018, 16:1722-1731.
Chowdary, P., et al., "Safety and pharmacokinetics of anti-TFPI antibody (concizumab) in healthy volunteers and patients with hemophilia: a randomized first human dose trial," Journal of Thrombosis and Haemostasis, 2015, 13:743-754.
Eichler, H., et al., "Concizumab (anti-TFPI) Exposure-Response Modeling in Patients with Hemophilia A," Blood, 2017, 130(Suppl 1):3672.
Fizika belka: Kurs lektcii's tcvetny'mi i stereoskopicheskimi illiustratciiami i zadachami: uchebnoe posobie / A.V. Finkel'shtei'n, O.B. Ptitcy'n,—4-e izdanie, ispr. i dop.—M.: KDU, 2012, p. 23 (English Translation).
Gennaro, AR., Remington's Pharmaceutical Sciences (2000) 20th Ed., LiPPincott Williams & Wilkins, Baltimore, MD, Cover and Table of Contents.
Hansen, L., et al., "Target-mediated clearance and bio-distribution of a monoclonal antibody against the Kunitz-type protease inhibitor 2 domain of Tissue Factor Pathway Inhibitor", Thrombosis Research, 2013, 133(3):464-471.
Hilden, I., et al., "Hemostatic Effect of a Monoclonal Antibody mAb 2021 Blocking the Interaction Between FXa and TFPI in a Rabbit Hemophilia Model," Blood, 2012, 119(24):5871-5878.
Holliger, P., and Hudson, P.J., "Engineered antibody fragments and the rise of single domains," Nature Biotechnology, 2005, 23(9):1126-1136.
International Preliminary Report on Patentability issued in PCT/IB2020/060571; mailed on May 27, 2022; 12 pp.
Janeway, C., and Travers, P., Immunobiology: The Immune System in Health and Disease, 3rd edition, 1999, Garland Publishing, Inc., 3:1-3:11.
Korte, W., et al., "The Potential Close Future of Hemophilia Treatment—Gene Therapy, TFPI Inhibition, Antithrombin Silencing, and Mimicking Factor VIII with an Engineered Antibody," Transfusion Medicine and Hemotherapy, 2018, 45:92-96.
Marks, J.D., et al., "By-passing Immunization Human Antibodies from V-gene Libraries Displayed on Phage," Journal of Molecular Biology, 1991, 222, 581-597.
Massimo F. et al., "Non-factor replacement therapy for haemophilia: a current update," Blood Transfusion = Transfusion Del Sangue 09, 2018, 16:5, 457-461.
Petersen, L.C., "Hemostatic Properties of a TFPI Antibody," Thrombosis Research, 2012, 129 (Suppl. 2):S44-S45.
Rudikoff, S., et al., "Single amino acid substitution altering antigen-binding specificity," Proceedings of the National Academy of Sciences USA, 1982, 79(6):1979-83.
Sheets, M. D., et al., "Efficient Construction of a Large Nonimmune Phage Antibody Library: The Production of High-Affinity Human Single-Chain Antibodies to Protein Antigens," Proceedings of the National Academy of Science, 1998, 95:6157-6162.
Sprecher, C.A., et al., "Molecular Cloning, Expression, and Partial Characterization of a Second Human Tissue-Factor-Pathway Inhibitor," Proceedings National Academy of Science, 1994, 91:3353-3357.
Vaughan, T. J., et al., "Human Antibodies with Sub-nanomolar Affinities Isolated from a Large Non-immunized Phage Display Library," Nature, 1996, 14:309-314.
Ward, S.E., et al., "Binding Activities of a Repertoire of Single Immunoglobulin Variable Domains Secreted from *Escherichia coli,*" 1989, Nature, 341:544-546.

(56) References Cited

OTHER PUBLICATIONS

Winckers, K., et al., "Increased tissue factor pathway inhibitor activity is associated with myocardial infarction in young women: results from the RATIO study," Journal of Thrombosis and Haemostasis, 2011, 9(11):2243-2250.
Yarilin, A.A., "Osnovy immunologii," M.: Meditsina, 1999, pp. 169-179 (English Translation).
Zhou, S., et al., "Comparative evaluation of disodium edetate and diethylenetriaminepentaacetic acid as iron chelators to prevent metal-catalyzed destabilization of a therapeutic monoclonal antibody," Journal of the American Pharmaceutical Association / Scientific Edition, American Pharmaceutical Association, US, 2010, 99(10):4239-4250.
Alhemo (concizumab-mtci), U.S. Prescribing Information, Jul. 2025, pp. 1-12, Retrieved on Sep. 5, 2025, https://www.novo-pi.com/alhemo.pdf.
Hemlibra (emicizumab-kxwh), U.S. Prescribing Information, Jul. 2025, pp. 1-26, Retrieved Sep. 5, 2025, https://www.gene.com/download/pdf/hemlibra_prescribing.pdf.
Hympavzi (marstacimab-hncq), U.S. Prescribing Information, Oct. 2024, pp. 1-30, Retrieved Sep. 5, 2025, https://labeling.pfizer.com/ShowLabeling.aspx?id=20916.
Matino, D., et al., "Efficacy and Safety of the Anti-Tissue Factor Pathway Inhibitor Marstacimab in Participants with Severe Hemophilia without Inhibitors: Results from the Phase 3 Basis Trial," 2023, Blood, 142:285-287.
Nayak, S., et al., "A Fixed (Weight-independent) Subcutaneous Once-Weekly Dose for Marstacimab, an Anti-TFPI Monoclonal Antibody for the Prophylactic Treatment of Hemophilia A and B," 2024, Blood, 144:1215.
Nayak, S., et al., "A Fixed (Weight-independent) Subcutaneous Once-Weekly Dose for Marstacimab, and Anti-TPFI Antibody for the Prophylactic Treatment of Hemophilia A and B," American Society of Hematology (ASH), Annual Meeting, Dec. 7-10, 2024, Poster No. 1215.
Nayak, S., et al., "Using a Systems Pharmacology Model of the Blood Coagulation Network to Predict the Effects of Various Therapies on Biomarkers," 2015, CPT Pharmacometrics System Pharmacology, 4:396-405.
Van De Weert, M., and Randolph, T.W., "Physical Instability of Peptides and Proteins." In Pharmaceutical Formulation Development of Peptides and Proteins, 2nd edition, eds., Hovgaard, L., et al., CRC Press, 2nd ed., 2012, p. 117-129.
Goswami, S., et al., "Developments and Challenges for mAb-Based Therapeutics" Antibodies, 2013, 2:452-500.

* cited by examiner

STABLE AQUEOUS ANTI-TFPI ANTIBODY FORMULATION

CROSS-REFERENCE TO RELATED APPLICATIONS

This application is the U.S. National Phase of International Application No. PCT/IB2020/060571, filed Nov. 10, 2020, which claims the benefit of U.S. Provisional Application Nos. 62/934,781, filed Nov. 13, 2019, and 63/081,409, filed Sep. 22, 2020, which are hereby incorporated by reference in their entirety.

REFERENCE TO SEQUENCE LISTING

This application is being filed electronically via EFS-Web and includes an electronically submitted sequence listing in .txt format. The .txt file contains a sequence listing entitled "PC72541A_Seq_Listing_ST25.txt" created on Oct. 13, 2020, and having a size of 42,550 bytes. The sequence listing contained in this .txt file is part of the specification and is hereby incorporated by reference in its entirety.

FIELD OF THE INVENTION

The present invention relates to the field of pharmaceutical formulations of antibodies. Specifically, the present invention relates to a stable liquid antibody formulation and its pharmaceutical preparation and use.

BACKGROUND

Antibody preparations intended for therapeutic or prophylactic use require stabilizers to prevent loss of activity or structural integrity of the protein due to the effects of denaturation, deamidation, oxidation or aggregation over a period of time during storage and transportation prior to use. These problems are exacerbated at the high concentrations of antibody often desired for therapeutic administration. A large number of formulation options are available, but not one approach or system is suitable for all proteins (See e.g., Wang et al., *J. Pharm Sci.* 96:1-26(2007)).

A major aim in the development of antibody formulations is to maintain antibody, solubility, stability and potency of its antigen binding. For an antibody to remain biologically active, a formulation must preserve the conformational integrity of at least a core of the antibody's antigen-binding amino acids. It is also particularly desirable to avoid aggregates and particulates in solution which would require sterile filtration before use for intravenous or subcutaneous injection and limit route of administration. Salts, surfactants, pH and tonicity agents such as sugars can be used to overcome aggregation or denaturation problems. Formulation of antibody preparations requires careful selection of these factors among others to avoid denaturation of the protein and loss of antigen-binding activity. Accordingly, there is a need for a stable aqueous antibody formulation which stably supports high concentrations of bioactive antibody in solution and is suitable for parenteral administration, including intravenous, intraocular, intravitreal, intraarterial, intrathecal, intraventricular, intraurethral, intrasternal, intracranial, intramuscular, intra-ossial, intraperitoneal, intradermal or subcutaneous injection.

It has been shown that Tissue Factor Pathway Inhibitor (TFPI) antibodies are useful in the treatment and prevention of blood coagulation deficiencies or bleeding disorders, such as hemophilia A and B (see for example, US 2017/0073428).

While liquid antibody formulations are known in the art (see, for example, WO2006/096491, WO 2010/032220, WO2013/186719, US 2009/0110681, US 2017/0360929, and US 2018/0000933), there is a need to provide a stable aqueous preparation of a TFPI antibody in order to meet the medical need of patients suffering blood coagulation deficiencies or bleeding disorders.

All publications, patents, and patent applications cited herein are hereby incorporated by reference herein in their entirety for all purposes to the same extent as if each individual publication, patent, and patent application were specifically and individually indicated to be so incorporated by reference. In the event that one or more of the incorporated literatures and similar materials differs from or contradicts this application, including but not limited to defined terms, term usage, described techniques, or the like, this application controls.

SUMMARY OF THE INVENTION

Stable aqueous pharmaceutical formulations with an extended shelf life comprising a Tissue Factor Pathway Inhibitor (TFPI) antibody (also known as anti-TFPI antibody) are provided. It is demonstrated that the formulation of the present invention with high TFPI antibody concentration is stable (e.g., having low levels of % HMMS (High Molecular Mass Species), % LMMS (Low Molecular Mass Species), % fragment, and oxidation) and hence suitable for parenteral administration.

Disclosed and exemplified herein are formulations for antibodies (including antigen-binding fragments thereof) that bind to the Tissue Factor Pathway Inhibitor (TFPI). Those skilled in the art will recognize or be able to ascertain using no more than routine experimentation, many equivalents to the specific embodiments of the invention described herein. Such equivalents are intended to be encompassed by the following embodiments (E).

E1. A formulation comprising: about 15 mg/mL to about 250 mg/mL of an antibody that specifically binds to Tissue Factor Pathway Inhibitor (TFPI), a buffer, a polyol, a surfactant, and a chelating agent, wherein the formulation has a pH at about 5.0 to about 6.0.

E2. A formulation comprising: about 15 mg/mL to about 250 mg/mL of an antibody that specifically binds to an epitope in Kunitz Domain 2 (K2) of Tissue Factor Pathway Inhibitor (TFPI), a buffer, a polyol, a surfactant, and a chelating agent, wherein the formulation has a pH at about 5.0 to about 6.0, and wherein the epitope comprises residues Ile105, Arg107, and Leu131, according to the numbering of SEQ ID NO: 2.

E3. The formulation as set forth in any one of E1-E2, wherein the buffer is selected from the group consisting of: acetate, succinate, gluconate, citrate, histidine, acetic acid, phosphate, phosphoric acid, ascorbate, tartartic acid, maleic acid, glycine, lactate, lactic acid, ascorbic acid, imidazole, bicarbonate and carbonic acid, succinic acid, sodium benzoate, benzoic acid, gluconate, edetate, acetate, malate, imidazole, tris, phosphate, and mixtures thereof.

E4. The formulation as set forth in E3, wherein the buffer is histidine.

E5. The formulation as set forth in E3, wherein the buffer is succinate.

E6. The aqueous formulation as set forth in any one of E1-E5, wherein the concentration of the buffer is about 0.1 mM to about 100 mM.

E7. The formulation as set forth in E6, wherein the concentration of the buffer is about 1 mM to about 40 mM or about 10 mM to about 40 mM.

E8. The formulation as set forth in E7, wherein the concentration of the buffer is about 10 mM, about 20 mM or about 40 mM.

E9. The formulation as set forth in E8, wherein the concentration of the buffer is about 20 mM.

E10. The formulation as set forth in any one of E1-E9, wherein the polyol is selected from the group consisting of mannitol, trehalose, sorbitol, erythritol, isomalt, lactitol, maltitol, xylitol, glycerol, lactitol, propylene glycol, polyethylene glycol, inositol, fructose, glucose, mannose, sucrose, sorbose, xylose, lactose, maltose, sucrose, dextran, pullulan, dextrin, cyclodextrins, soluble starch, hydroxyethyl starch, water-soluble glucans, or mixtures thereof.

E11. The formulation as set forth in E10, wherein the polyol is sucrose or trehalose.

E12. The formulation as set forth in any one of E1-E11, wherein the concentration of the polyol is about 1 mg/mL to about 300 mg/mL.

E13. The formulation as set forth in E12, wherein the concentration of the polyol is about 1 mg/mL to about 120 mg/mL, about 50 mg/mL to about 120 mg/mL, or about 60 mg/mL to about 110 mg/m L.

E14. The formulation as set forth in E13, wherein the concentration of the polyol is about 64 mg/mL, about 85 mg/mL or about 106 mg/mL.

E15. The formulation as set forth in E1-E14 wherein the concentration of the polyol is about 85 mg/mL.

E16. The formulation as set forth in any one of E1-E15, wherein the surfactant is selected from the group consisting of a polysorbate, poloxamer, triton, sodium dodecyl sulfate, sodium laurel sulfate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine, myristamidopropyl-dimethylamine, palmidopropyl-dimethylamine, isostearamidopropyl-dimethylamine, sodium methyl cocoyl-taurate, disodium methyl oleyl-taurate, dihydroxypropyl PEG 5 linoleammonium chloride, polyethylene glycol, polypropylene glycol, polysorbate 20, polysorbate 21, polysorbate 40, polysorbate 60, polysorbate 61, polysorbate 65, polysorbate 80, polysorbate 81, polysorbate 85, PEG3350 and mixtures thereof.

E17. The formulation as set forth in E16, wherein the surfactant is polysorbate 80.

E18. The formulation as set forth in any one of E1-E17, wherein the concentration of the surfactant is about 0.01 mg/mL to about 10 mg/mL, about 0.05 mg/mL to about 5 mg/mL, about 0.1 mg/mL to about 1 mg/mL or about 0.1 mg/ml to about 0.5 mg/mL.

E19. The formulation as set forth in E18 wherein the concentration of the surfactant is about 0.1 mg/ml, about 0.2 mg/mL or about 0.3 mg/mL.

E20. The formulation as set forth in E19, wherein the concentration of the surfactant is about 0.2 mg/mL.

E21. The formulation as set forth in any one of E1-E20, wherein the formulation does not contain any surfactant (e.g., polysorbate 80).

E22. The formulation as set forth in any one of E1-E21, wherein the chelating agent is selected from the group consisting of ethylenediaminetetraacetic acid (EDTA), diethylenetriamine pentaacetic acid 5 (DTPA), nitrilotriacetic acid (NTA), N-2-acetamido-2-iminodiacetic acid (ADA), bis(aminoethyl)glycolether, N, N, N', N'-tetraacetic acid (EGTA), trans-diaminocyclohexane tetraacetic acid (DCTA), glutamic acid, and aspartic acid, N-hydroxyethyliminodiacetic acid (HIMDA), N,N-bis-hydroxyethylglycine (bicine) and N-(trishydroxymethylmethyl) 10 glycine (tricine), glycylglycine, sodium desoxycholate, ethylenediamine, propylenediamine, diethylenetriamine, triethylenetetraamine (trien), disodium edetate dihydrate (or disodium EDTA dihydrate or EDTA disodium salt), calcium EDTA oxalic acid, malate, citric acid, citric acid monohydrate, and trisodium citrate-dihydrate, 8-hydroxyquinolate, amino acids, histidine, cysteine, methionine, peptides, polypeptides, and proteins and mixtures thereof.

E23. The formulation as set forth in E22, wherein the chelating agent is disodium edetate dihydrate.

E24. The formulation as set forth in any one of E1-E23, wherein the concentration of the chelating agent is from about 0.01 mg/mL to about 50 mg/mL, from about 0.01 mg/mL to about 10 mg/mL, from about 0.01 mg/mL to about 1 mg/mL, or about 0.02 mg/m L to about 0.08 mg/m L.

E25. The formulation as set forth in E24, wherein the concentration of the chelating agent is about 0.038 mg/mL, about 0.05 mg/mL or about 0.063 mg/mL.

E26. The formulation as set forth in E25, wherein the concentration of the chelating agent is about 0.05 mg/mL.

E27. The formulation as set forth in any one of E1-E26, wherein the formulation has a pH of about 5.0 to 6.6 or about 5.2 to 6.4.

E28. The formulation as set forth in E27, wherein the formulation has a pH of about 5.2, 5.8 or 6.4.

E29. The formulation as set forth in E27, wherein the formulation has a pH of about 5.5 or 5.8.

E30. The formulation as set forth in any one of E1-E29, wherein the antibody does not bind to Kunitz Domain 1 (K1) of TFPI.

E31. The formulation as set forth in any one of E2-E30, wherein the epitope further comprises residues Cys106, Gly108, Cys130, Leu131, and Gly132, according to the numbering of SEQ ID NO: 2.

E32. The formulation as set forth in any one of E2-E31, wherein the epitope further comprises Asp102, Arg112, Tyr127, Gly129, Met134, and Glu138, according to the numbering of SEQ ID NO: 2.

E33. The formulation as set forth in any one of E2-E32, wherein the epitope does not comprise: E100, E101, P103, Y109, T111, Y113, F114, N116, Q118, Q121, C122, E123, R124, F125, K126, and L140, according to the numbering of SEQ ID NO: 2.

E34. The formulation as set forth in any one of E2-E32, wherein the epitope does not comprise: D31, D32, P34, C35, K36, E100, E101, P103, Y109, K126, and G128, according to the numbering of SEQ ID NO: 2.

E35. The formulation as set forth in any one of E1-E34, wherein the antibody comprises a heavy chain variable region (VH) comprising:

(a) a VH complementarity determining region one (CDR-H1) comprising the amino acid sequence of SEQ ID NO: 13.

(b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15.

E36. The formulation as set forth in any one of E1-E35, wherein the antibody comprises a VH comprising an amino acid sequence at least 90%, at least 95%, or at least 99% identical to an amino acid sequence selected from the group consisting of SEQ ID NOs: 16, 18, and 20.

E37. The formulation as set forth in any one of E1-E36, wherein the antibody comprises a VH comprising an amino acid sequence selected from the group consisting of SEQ ID NOs: 16, 18, and 20.

E38. The formulation as set forth in any one of E1-E37, wherein the antibody comprises a VH comprising the amino acid sequence of SEQ ID NO: 16.

E39. The formulation as set forth in any one of E1-E37, wherein the antibody comprises a VH comprising the amino acid sequence of SEQ ID NO: 18.

E40. The formulation as set forth in any one of E1-E37, wherein the antibody comprises a VH comprising the amino acid sequence of SEQ ID NO: 20.

E41. The formulation as set forth in any one of E1-E40, wherein the antibody comprises a light chain variable region (VL) comprising:

(a) a VL complementarity determining region one (CDR-L1) comprising the amino acid sequence of SEQ ID NO: 8.

(b) a VL complementarity determining region two (CDR-L2) comprising the amino acid sequence of SEQ ID NO: 9; and (c) a VL complementarity determining region three (CDR-L3) comprising the amino acid sequence of SEQ ID NO: 10.

E42. The formulation as set forth in any one of E1-E41, wherein the antibody comprises a VL comprising an amino acid sequence at least 90%, at least 95%, or at least 99% identical to SEQ ID NO: 11.

E43. The formulation as set forth in any one of E1-E42, wherein the antibody comprises a VL comprising the amino acid sequence of SEQ ID NO: 11.

E44. The formulation as set forth in any one of E1-E43, wherein the antibody comprises a heavy chain comprising the amino acid sequence of SEQ ID NO: 17.

E45. The formulation as set forth in any one of E1-E43, wherein the antibody comprises a heavy chain comprising the amino acid sequence of SEQ ID NO: 19.

E46. The formulation as set forth in any one of E1-E43, wherein the antibody comprises a heavy chain comprising the amino acid sequence of SEQ ID NO: 21.

E47. The formulation as set forth in any one of E1-E46, wherein the antibody comprises a light chain comprising the amino acid sequence of SEQ ID NO: 12.

E48. The formulation as set forth in any one of E1-E47, wherein the antibody comprises:

(i) a heavy chain variable region (VH) comprising: (a) a VH complementarity determining region one (CDR-H1) comprising the amino acid sequence of SEQ ID NO: 13; (b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15, and (ii) a light chain variable region (VL) comprising: (a) a VL complementarity determining region one (CDR-L1) comprising the amino acid sequence of SEQ ID NO: 8; (b) a VL complementarity determining region two (CDR-L2) comprising the amino acid sequence of SEQ ID NO: 9; and (c) a VL complementarity determining region three (CDR-L3) comprising the amino acid sequence of SEQ ID NO: 10.

E49. The formulation as set forth in E48, wherein the antibody comprises a VH comprising the amino acid sequence of SEQ ID NO: 18, and a VL comprising the amino acid sequence of SEQ ID NO: 11.

E50. The formulation as set forth in any one of E1-E49, wherein the antibody comprises the VH sequence encoded by the insert present in the plasmid deposited under ATCC Accession No. PTA-122329.

E51. The formulation as set forth in any one of E1-E50, wherein the antibody comprises the VL sequence encoded by the insert present in the plasmid deposited under ATCC Accession No. PTA-122328.

E52. The formulation as set forth in any one of E1-E51, wherein the antibody comprises a sequence encoded by the insert present in the plasmid deposited under ATCC Accession No. PTA-122329 and a sequence encoded by the insert present in the plasmid deposited under ATCC Accession No. PTA-122328.

E53. The formulation as set forth in any one of E1-E52, wherein the antibody comprises a heavy chain comprising the amino acid sequence of SEQ ID NO: 19, and comprises a light chain comprising the amino acid sequence of SEQ ID NO: 12.

E54. The formulation as set forth in E48, wherein the antibody comprises a VH comprising the amino acid sequence of SEQ ID NO: 16, and a VL comprising the amino acid sequence of SEQ ID NO: 11.

E55. The formulation as set forth in E54, wherein the antibody comprises a heavy chain comprising the amino acid sequence of SEQ ID NO: 17, and comprises a light chain comprising the amino acid sequence of SEQ ID NO: 12.

E56. The formulation as set forth in E48, wherein the antibody comprises a VH comprising the amino acid sequence of SEQ ID NO: 20, and a VL comprising the amino acid sequence of SEQ ID NO: 11.

E57. The formulation as set forth in E56, wherein the antibody comprises a heavy chain comprising the amino acid sequence of SEQ ID NO: 21, and comprises a light chain comprising the amino acid sequence of SEQ ID NO: 12.

E58. The formulation as set forth in any one of E1, E3-E29, wherein the antibody comprises a heavy chain comprising the amino acid sequence of SEQ ID NO: 23, and comprises a light chain comprising the amino acid sequence of SEQ ID NO: 22.

E59. The formulation as set forth in any one of E1, E3-E29, wherein the antibody comprises a heavy chain comprising the amino acid sequence of SEQ ID NO: 25, and comprises a light chain comprising the amino acid sequence of SEQ ID NO: 24.

E60. The formulation as set forth in any one of E1-E59, wherein the antibody has a serum half-life of at least 25 hours, at least 29 hours, at least 30 hours at least 35 hours, at least 40 hours, at least 50 hours, at least 55 hours, at least 60 hours, at least 65 hours, at least 70 hours, at least 75 hours, at least 80 hours, at least 85 hours, at least 90 hours, at least 95 hours, at least 100 hours, at least 105 hours, at least 110 hours, at least 115 hours, at least 120 hours or at least 125 hours.

E61. The formulation as set forth in any one of E1-E60, wherein the antibody has a binding affinity ($K_D$) of from about $5\times10^{-7}$M to about $5\times10^{-11}$ M.

E62. The formulation as set forth in any one of E1-E61, wherein the antibody has a subcutaneous (SC) bioavailability of at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, at least 90%, at least 95, or at least 99% relative to intravenous bioavailability.

E63. The formulation as set forth in any one of E1-E62, wherein the concentration of the antibody is about 20 mg/mL, 25 mg/mL, 50 mg/mL, 75 mg/mL, 100 mg/ml, 125 mg/ml, 150 mg/mL, 175 mg/mL, 200 mg/ml, 225 mg/ml, or 250 mg/mL.

E64. An aqueous formulation comprising: about 150 mg/mL of an antibody that specifically binds to an epitope in Kunitz Domain 2 (K2) of Tissue Factor Pathway Inhibitor (TFPI), about 20 mM succinate or histidine buffer; about 85 mg/mL sucrose or trehalose; about 0.2 mg/mL polysorbate 80 or polysorbate 20; about 0.05 mg/mL disodium edetate dihydrate or ethylenediaminetetraacetic acid (EDTA); wherein the antibody comprises a heavy chain variable region comprising the amino acid sequence of SEQ ID NO: 18, and a light chain variable region comprising the amino acid sequence of SEQ ID NO: 11; and wherein the formulation has a pH of about 5.5 or 5.8.

E65. A pharmaceutical formulation comprising: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, 0.05 mg/mL disodium edetate dihydrate, wherein the antibody comprises a heavy chain variable region comprising the amino acid sequence of SEQ ID NO: 18, and a light chain variable region comprising the amino acid sequence of SEQ ID NO: 11; and wherein the formulation has a pH of 5.8.

E66. A pharmaceutical formulation comprising: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, 0.05 mg/mL disodium edetate dihydrate, wherein the antibody comprises a heavy chain comprising the amino acid sequence of SEQ ID NO: 19, and comprises a light chain comprising the amino acid sequence of SEQ ID NO: 12; and wherein the formulation has a pH of 5.8.

E67. A pharmaceutical formulation comprising: about 50 mg/mL to about 250 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, 0.05 mg/mL disodium edetate dihydrate, wherein the antibody comprises a heavy chain comprising the amino acid sequence of SEQ ID NO: 23, and comprises a light chain comprising the amino acid sequence of SEQ ID NO: 22; and wherein the formulation has a pH of 5.8.

E68. A pharmaceutical formulation comprising: about 50 mg/mL to about 250 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, 0.05 mg/mL disodium edetate dihydrate, wherein the antibody comprises a heavy chain comprising the amino acid sequence of SEQ ID NO: 25, and comprises a light chain comprising the amino acid sequence of SEQ ID NO: 24; and wherein the formulation has a pH of 5.8.

E69. A pharmaceutical formulation comprising: 150 mg/mL of an antibody that specifically binds to an epitope in Kunitz Domain 2 (K2) of Tissue Factor Pathway Inhibitor (TFPI), 10 mM histidine buffer, 64 mg/mL sucrose, 0.1 mg/mL polysorbate 80, 0.038 mg/mL disodium edetate dihydrate, wherein the antibody comprises a heavy chain variable region comprising the amino acid sequence of SEQ ID NO: 18, and a light chain variable region comprising the amino acid sequence of SEQ ID NO: 11; and wherein the formulation has a pH of 6.4.

E70. A pharmaceutical formulation comprising: 150 mg/mL of an antibody that specifically binds to an epitope in Kunitz Domain 2 (K2) of Tissue Factor Pathway Inhibitor (TFPI), 40 mM histidine buffer, 106 mg/mL sucrose, 0.3 mg/mL polysorbate 80, 0.063 mg/mL disodium edetate dihydrate, wherein the antibody comprises a heavy chain variable region comprising the amino acid sequence of SEQ ID NO: 18, and a light chain variable region comprising the amino acid sequence of SEQ ID NO: 11; and wherein the formulation has a pH of 5.2.

E71. A pharmaceutical formulation comprising: 150 mg/mL of an antibody that specifically binds to an epitope in Kunitz Domain 2 (K2) of Tissue Factor Pathway Inhibitor (TFPI), 10 mM histidine buffer, 64 mg/mL sucrose, 0.1 mg/mL polysorbate 80, 0.038 mg/mL disodium edetate dihydrate, wherein the antibody comprises a heavy chain variable region comprising the amino acid sequence of SEQ ID NO: 18, and a light chain variable region comprising the amino acid sequence of SEQ ID NO: 11; and wherein the formulation has a pH of 5.2.

E72. A pharmaceutical formulation comprising: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.05 mg/mL disodium edetate dihydrate, wherein the antibody comprises a heavy chain variable region comprising the amino acid sequence of SEQ ID NO: 18, and a light chain variable region comprising the amino acid sequence of SEQ ID NO: 11; and wherein the formulation has a pH of 5.8.

E73. The pharmaceutical formulation as set forth in E72, wherein the formulation does not comprise a surfactant (e.g., polysorbate 80).

E74. The formulation as set forth in any one of E1-E73, wherein the formulation has a shelf life of at least about 1 month, about 3 months, about 4 months, about 6 months, about 12 months, about 24 months, about 36 months, about 48 months, or about 60 months (e.g., at about −20° C., at about 5° C., at about 25° C., or at about 40° C.).

E75. The formulation as set forth in any one of E1-E74, wherein the formulation is an aqueous formulation.

E76. The formulation as set forth in any one of E1-E75, wherein the formulation is a pharmaceutical formulation.

E77. A method of shortening bleeding time, comprising administering to a subject in need thereof a therapeutically effective amount of the formulation as set forth in any one of E1-E76.

E78. A method of treating or preventing a deficiency in blood coagulation or a bleeding disorder, comprising administering to a subject in need thereof a therapeutically effective amount of the formulation as set forth in any one of E1-E76.

E79. A method of treating or preventing hemophilia A, B or C, comprising administering to a subject in need thereof a therapeutically effective amount of the formulation as set forth in any one of E1-E76.

E80. A method of treating or preventing von Willebrand Disease (vWD), comprising administering to a subject in need thereof a therapeutically effective amount of the formulation as set forth in any one of E1-E76.

E81. A method for reducing the activity of TFPI, comprising administering to a subject in need thereof a therapeutically effective amount of the formulation as set forth in any one of E1-E76.

E82. The method as set forth in any one of E77-E81, wherein the subject suffers from or is susceptible to a deficiency in blood coagulation or a bleeding disorder.

E83. The method as set forth in any one of E77-E82, wherein the subject suffers from or is susceptible to hemophilia A, B or C.

E84. The method as set forth in any one of E77-E83, wherein the subject suffers from or is susceptible to hemophilia A or B.

E85. The method as set forth in any one of E77-E82, wherein the subject suffers from or is susceptible to von Willebrand Disease (vWD).

E86. The method as set forth in any one of E77-E82, wherein the subject suffers from or is susceptible to a platelet disorder.

E87. The method as set forth in any one of E77-82, wherein the subject suffers from or is susceptible to a Factor VII deficiency.

E88. The method as set forth in any one of E77-E82, wherein the subject suffers from or is susceptible to a Factor XI deficiency.

E89. The method as set forth in any one of E77-E88, further comprising administering a clotting agent to the subject.

E90. The method as set forth in E89, wherein the clotting agent is selected from the group consisting of Factor Vila, Factor VIII, Factor IX, tranexamic acid and bypass agents (e.g., FEIBA).

E91. Use of the formulation of any one of E1-E76 in a method as set forth in any one of E77-E90.

E92. A formulation as set forth in any one of E1-E76 for use in a method as set forth in any one of E77-E90.

E93. A formulation comprising: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, 0.05 mg/mL disodium edetate dihydrate, for use in a method as set forth in any one of E77-E90, wherein the antibody comprises a heavy chain comprising the amino acid sequence of SEQ ID NO: 19, and comprises a light chain comprising the amino acid sequence of SEQ ID NO: 12, and wherein the formulation has a pH of 5.8.

E94. A pharmaceutical formulation consisting of: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, 0.05 mg/mL disodium edetate dihydrate, wherein the antibody comprises a heavy chain comprising the amino acid sequence of SEQ ID NO: 19, and comprises a light chain comprising the amino acid sequence of SEQ ID NO: 12; and wherein the formulation has a pH of 5.8.

DETAILED DESCRIPTION

Disclosed herein are stable aqueous pharmaceutical formulations with an extended shelf-life comprising a Tissue Factor Pathway Inhibitor (TFPI) antibody. The present application is based on the discovery that a formulation comprising histidine buffer and having pH 5.8 stably supports high concentrations of TFPI antibody.

In particular, it was demonstrated that anti-TFPI antibody stored in histidine-buffered aqueous formulation with pH 5.8 had low levels of degradation as measured by % high molecular mass species (% HMMS) using size exclusion-high performance liquid chromatography (SE-HPLC) (see Table 1). For example, at the intended storage condition of 5±3° C., the anti-TFPI antibody was stable for up to 24 months with little to no degradation observed (% HMMS ranged from 0.5 to 0.9). Although some degradation was observed at the thermal stress storage condition of 40° C./75% RH (% HMMS ranged from 0.9 to 1.2 at 1 month (i.e., 4 weeks) and from 1.5 to 2.4 at 3 months (i.e., 12 weeks)), this degradation was less than what was observed for other IgG1 antibodies such as anti-VEGF antibody (see Table 9; data for anti-VEGF antibody obtained from Table 11 of US 2018/0000933). In particular, the amount of high molecular mass species (% HMMS) for anti-VEGF antibody stored in histidine-buffered formulation having pH 5.8 at 40° C. for 1 month (i.e., 4 weeks) was 3.1 (as compared to 0.9 to 1.2 for anti-TFPI antibody), and stored for 3 months (i.e., 12 weeks) was 5.6 (as compared to 1.5 to 2.4 for anti-TFPI antibody). Thus, histidine-buffered formulation at pH 5.8 retards degradation, reduces aggregate formation and improves stability of anti-TFPI antibody as compared to anti-VEGF antibody. This result was surprising and unexpected.

Accordingly, in one aspect, provided is a formulation comprising: about 15 mg/mL to about 250 mg/mL of a Tissue Factor Pathway Inhibitor (TFPI) antibody, a buffer, a polyol, a surfactant, a chelating agent, and wherein the formulation has a pH at about 5.0 to about 6.0. For example, in some embodiments, provided is a formulation comprising: about 15 mg/mL to about 250 mg/mL of TFPI antibody (e.g., anti-TFPI antibody), about 1 mM to about 40 mM of a buffer (e.g., histidine buffer), about 1 mg/mL to about 300 mg/mL of a polyol (e.g., sucrose), about 0.01 mg/mL to about 10 mg/mL of a surfactant (e.g., polysorbate 80), about 0.01 mg/mL to about 50.0 mg/mL of a chelating agent (e.g., disodium edetate dihydrate), wherein the formulation has a pH at about 5.0 to about 6.0. In some embodiments, the antibody concentration is about 15 mg/mL to about 250 mg/m L. In other embodiments, the antibody concentration is about 100 mg/mL, about 115 mg/mL, about 150 mg/mL or 158 mg/mL.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

The following terms, unless otherwise indicated, shall be understood to have the following meanings: the term "isolated molecule" or "purified molecule" (where the molecule is, for example, a polypeptide, a polynucleotide, or an antibody) is a molecule that by virtue of its origin or source of derivation: (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the term "formulation" as it relates to an antibody is meant to describe an antibody preparation in such form as to permit the biological activity of the antibody to be effective.

The terms "pharmaceutical composition" or "pharmaceutical formulation" refer to preparations of an antibody in combination with a pharmaceutically acceptable carrier/excipient. As used herein, an "aqueous formulation" refers to a formulation that contains water as a component.

"Pharmaceutically acceptable carriers/excipients" (vehicles, additives) are those, which can safely be administered to a subject to provide an effective dose of the active ingredient employed. The term "excipient" or "carrier" as used herein refers to an inert substance, which is commonly used as a diluent, vehicle, preservative, binder or stabilizing agent for drugs. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000). As used herein, the term "diluent" refers to a pharmaceutically acceptable (safe and non-toxic for administration to a human) solvent and is useful for the preparation of the formulations described herein. Exemplary diluents include, but are not limited to, sterile water and bacteriostatic water for injection (BWFI).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding fragment/portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')2, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "ABMT™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues. As used herein, the term "human antibody" is intended to include antibodies having variable and constant regions derived from human germline immunoglobulin sequences. This definition of a human antibody includes antibodies comprising at least one human heavy chain polypeptide or at least one human light chain polypeptide. The human antibodies of the invention may include amino acid residues not encoded by human germ line immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J Immunol. 138: 4534-4538 (1987), and Brown et al. Cancer Res. 47: 3577-3583 (1987). Other references describe rodent CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e. g., does not trigger complement lysis). See, e. g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160.

As used herein, the term "recombinant antibody" is intended to include all antibodies that are prepared, expressed, created or isolated by recombinant means, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes or antibodies prepared, such recombinant human antibodies can be subjected to in vitro mutagenesis.

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to TFPI, e.g., the antibodies compete for binding to the antigen.

The term "antagonist antibody" refers to an antibody that binds to a target and prevents or reduces the biological effect of that target. In some embodiments, the term can denote an antibody that reduces the target, e.g., TFPI, to which it is bound from performing a biological function.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a TFPI epitope is an antibody that binds this epitope sequence with greater affinity, avidity, more readily, and/or with greater duration than it binds to other sequences. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A variety of assay formats may be used to select an antibody or peptide that specifically binds a molecule of interest. For example, solid-phase ELISA immunoassay, immunoprecipitation, Biacore™ (GE Healthcare, Piscataway, NJ), KinExA, fluorescence-activated cell sorting (FACS), Octet™ (FortéBio, Inc., Menlo Park, CA) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background. Also, an antibody is said to "specifically bind" an antigen when the equilibrium dissociation constant ($K_D$) is ≤7 nM.

The term "binding affinity" is herein used as a measure of the strength of a non-covalent interaction between two molecules, e.g., and antibody, or fragment thereof, and an antigen. The term "binding affinity" is used to describe monovalent interactions (intrinsic activity).

Binding affinity between two molecules, e.g., an antibody, or fragment thereof, and an antigen, through a monovalent interaction may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1\times10^{-6}$M or more, more preferably $1\times10^{-5}$ M or more, more preferably $1\times10^{-4}$ M or more, more preferably $1\times10^{-3}$ M or more, even more preferably $1\times10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold or greater than its affinity for binding to another non-TFPI molecule.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, the term "Tissue Factor Pathway Inhibitor or TFPI" refers to any form of TFPI and variants thereof that retain at least part of the activity of TFPI. TFPI is a multi-valent Kunitz domain containing protease inhibitor. Exemplary sequences of human, mouse, cynomolgus monkey, rabbit, and rat TFPI are provided in Table 20. Human TFPI is an extracellular glycoprotein with two predominant forms, TFPI-alpha and TFPI-beta. TFPI alpha, which is a 276 amino acid glycosylated protein (MW 43 kD) is the largest form of TFPI and consists of three Kunitz like domains and a basic carboxy terminal region. Alternative splicing produces TFPI-beta, which contains Kunitz Domain 1 (K1) and Kunitz Domain 2 (K2), but contains an alternative C-terminal portion lacking Kunitz domain 3 (K3) and the basic region. TFPI-beta is anchored to cell membranes through post-translational modification with a glycosylphosphatidylinositol (GPI) anchor.

The primary targets of TFPI are the proteases Factor Xa (FXa) and Factor Vila (FVIIa), which are key factors in the initiation stage of the coagulation cascade. Biochemical analysis has revealed that K2 is the inhibitor of FXa, while K1 inhibits FVIIa-Tissue Factor complex. The role of K3 is unclear as it does not seem to have direct protease inhibitory activity, but may serve as a recognition site for the co-factor Protein S. The C-terminal domain, unique to TFPI-alpha, may be involved in the recognition of prothrombinase on the platelet surface.

Kunitz domain 1 (K1) corresponds to amino acid residues 26-76 of SEQ ID NO: 2, and Kunitz domain 2 (K2) corresponds to residues 91 to 147 of SEQ ID NO: 2. The K1 and K2 domains from other TFPI homologs, isoforms, variants, or fragments can be identified by sequence alignment or structural alignment against SEQ ID NO: 2.

The TFPI of the instant disclosure includes any naturally occurring form of TFPI which may be derived from any suitable organism. For example, TFPI may be a mammalian TFPI, such as human, mouse, rat, non-human primate, bovine, ovine, canine, feline, or porcine TFPI. In certain embodiments, the TFPI is human TFPI. The TFPI may be a mature form of TFPI (i.e., a TFPI protein that has undergone post-translational processing within a suitable cell). Such a mature TFPI protein may, for example, be glycosylated.

The TFPI of the instant disclosure includes any functional fragments or variants derived from a naturally occurring TFPI. A functional fragment of TFPI can be any part or portion of TFPI that retains the activity of a TFPI, such as the ability to inhibit Factor Xa (FXa), to inhibit the activity of FVIIa-tissue factor complex, and/or to function as a negative regulator of coagulation or hemostasis. For example, a functional fragment may comprise a Kunitz domain, such as the K1 domain, K2 domain, or both K1 and K2 domains of TFPI.

A functional variant can comprise one or more mutations as compared to a naturally occurring TFPI, and still retain the activity of a naturally occurring TFPI, such as the ability to inhibit Factor Xa (FXa), or the ability to inhibit the activity of FVIIa-tissue factor complex. For example, a variant may have various degrees of sequence identity to SEQ ID NOs: 1, 2, 3, 4, 5, 6, or 7, such as at least 60%, 70%, 80%, 85%, 90%, 91%, 92%, 93%, 94%, 95%, 96%, 97%, 98% or 99% A identical to the sequence recited in SEQ ID NO: 1, SEQ ID NO: 2, SEQ ID NO: 3, SEQ ID NO: 4, SEQ ID NO: 5, SEQ ID NO: 6, or SEQ ID NO: 7.

The TPFI fragments, variants, isoforms and homologs of the invention should maintain important epitope residues (such as Ile105, Arg107, and Leu131, if TFPI-23 and TFPI-106 antibodies are used) as described herein. In addition, the TFPI may comprise five or more, eight or more, ten or more, twelve or more or fifteen or more surface accessible residues of the K2 domain of TFPI. A surface accessible residue is a residue having more than 40% relative accessibility.

For example, for the K2 domain of TFPI (see, e.g., SEQ ID NO: 2), the following amino acid residues have a greater than 40% relative accessibility: 94-95, 98, 100-110, 118-121, 123-124, 131, 134, 138-142 and 144-145. The TFPI may comprise five or more, eight or more, ten or more, twelve or more or fifteen or more of these residues, such as a fragment of TFPI that includes five or more, eight or more, ten or more, twelve or more or fifteen or more of these residues.

Specific amino acid residue positions in TFPI are numbered according to SEQ ID NO: 2 (human TFPIα K1K2K3). However, the present invention is not limited to SEQ ID NO: 2. Corresponding residues from other TFPI homologs, isoforms, variants, or fragments can be identified according to sequence alignment or structural alignment that is known in the art. For example, alignments can be done by hand or by using well-known sequence alignment programs such as ClustalW2, or "BLAST 2 Sequences" using default parameters. For example, Arg107 of SEQ ID NO: 2 corresponds to Arg104 of Mouse TFPI K1K2 (SEQ ID NO: 4).

As used herein, a "TFPI antagonist antibody" (interchangeably termed "TFPI antibody" or "anti-TFPI antibody") refers to an antibody that is able to bind to TFPI and inhibit TFPI biological activity and/or downstream pathway(s) mediated by TFPI signaling. A TFPI antagonist antibody encompasses antibodies that block, antagonize, suppress or reduce (including significantly) TFPI biological activity, including downstream pathways mediated by TFPI signaling, such as ligand binding and/or elicitation of a cellular response to TFPI. For purpose of the present invention, it will be explicitly understood that the term "TFPI antagonist antibody" encompasses all the previously identified terms, titles, and functional states and characteristics whereby the TFPI itself, a TFPI biological activity (including but not limited to its ability to mediate any aspect of blood coagulation), or the consequences of the biological activity, are substantially nullified, decreased, or neutralized in any meaningful degree. In some embodiment, a TFPI antagonist antibody binds TFPI and prevents TFPI binding to and/or inhibition of Tissue Factor (TF)/Factor Vila complex. In other embodiments, a TFPI antibody binds TFPI and prevents TFPI binding to and/or inhibition of Factor Xa. Examples of TFPI antagonist antibodies are provided herein.

An "effective amount" of drug, formulation, compound, or pharmaceutical composition is an amount sufficient to effect beneficial or desired results including clinical results such as alleviation or reduction of the targeted pathologic condition. An effective amount can be administered in one or more administrations. For purposes of this invention, an effective amount of drug, compound, or pharmaceutical composition is an amount sufficient to treat, ameliorate, or reduce the intensity of the targeted pathologic condition. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "therapeutically effective amount" refers to an amount effective, at dosages and for periods of time necessary, to achieve the desired therapeutic result, which in the context of anti-TFPI antibodies includes treatment or prophylactic prevention of the targeted pathologic condition, for example bleeding disorders such as hemophilia A, B, or C. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Likewise, a therapeutically effective amount of the antibody or antibody portion may vary according to factors such as the disease state, age, sex, and weight of the individual, the ability of the antibody or antibody portion to elicit a desired response in the individual, and the desired route of administration of the antibody formulation. A therapeutically effective amount is also one in which any toxic or detrimental effects of the antibody or antibody portion are outweighed by the therapeutically beneficial effects.

Therapeutically effective amounts for anti-TFPI antibodies are described, for example, in PCT/IB2019/058597 filed Oct. 9, 2019 (which claims priority to U.S. 62/802,401 and U.S. 62/744,481), which is incorporated herein in its entirety. In some embodiments, the therapeutically effective amount includes an initial dose of about 300 mg followed by subsequent weekly (i.e., once a week) doses of about 150 mg. In some embodiments, the therapeutically effective amount includes an initial dose of about 150 mg and subsequent weekly (i.e., once a week) doses of about 150 mg. In some embodiments, the therapeutically effective amount includes an initial dose of about 300 mg and subsequent weekly (i.e., once a week) doses of about 300 mg. In some embodiments, the therapeutically effective amount includes an initial dose of about 450 mg and subsequent weekly (i.e., once a week) doses of about 450 mg.

As used herein, the term "treatment" refers to both therapeutic treatment and prophylactic or preventative measures, wherein the object is to prevent or slow down (lessen) the targeted pathologic condition (e.g., any condition that would benefit from treatment with the antibody). This includes chronic and acute disorders or diseases including those pathological conditions which predispose the mammal to the disorder in question. Those in need of treatment include those already with the condition as well as those prone to have the condition or those in whom the condition is to be prevented. As used herein, "treatment" is an approach for obtaining beneficial or desired clinical results including, but not limited to, one or more of the following: including lessening severity, alleviation of one or more symptoms associated with the pathologic condition.

As used herein, the term "subject" or "individual" for purposes of treatment includes any subject, and preferably is a subject who is in need of the treatment of the targeted pathologic condition (e.g., hemophilia). For purposes of prevention, the subject is any subject, and preferably is a subject that is at risk for, or is predisposed to, developing the targeted pathologic condition. The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the term "polynucleotide" or "nucleic acid", used interchangeably herein, means a polymeric form of nucleotides either ribonucleotides or deoxynucleotides or a modified form of either type of nucleotide and may be single and double stranded forms. A "polynucleotide" or a "nucleic acid" sequence encompasses its complement unless otherwise specified. As used herein, the term "isolated polynucleotide" or "isolated nucleic acid" means a polynucleotide of genomic, cDNA, or synthetic origin or some combination thereof, which by virtue of its origin or source of derivation, the isolated polynucleotide has one to three of the following: (1) is not associated with all or a portion of a polynucleotide with which the "isolated polynucleotide" is found in nature, (2) is operably linked to a polynucleotide to which it is not linked in nature, or (3) does not occur in nature as part of a larger sequence.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

When introducing elements of the present invention or the preferred embodiment(s) thereof, the articles "a", "an", "the" and "said" are intended to mean that there are one or more of the elements. The terms "comprising", "comprise", "comprises", "including" and "having" are intended to be inclusive and mean that there may be additional elements other than the listed elements. It is understood that wherever embodiments are described herein with the language "comprising," otherwise analogous embodiments described in terms of "consisting of" and/or "consisting essentially of" are also provided.

Unless otherwise defined, all technical and scientific terms used herein have the same meaning as commonly understood by one of ordinary skill in the art to which this invention belongs. In case of conflict, the present specification, including definitions, will control. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

Anti-TFPI Antibody Formulation

The present application is based on the surprising and unexpected observation that a formulation comprising histidine buffer and having pH 5.8 retards degradation, reduces aggregate formation and improves stability of anti-TFPI antibody as compared to other IgG1 antibodies such as the anti-VEGF antibody.

Accordingly, in one aspect, provided herein is a formulation comprising: about 15 mg/mL to about 250 mg/mL of a Tissue Factor Pathway Inhibitor (TFPI) antibody, a buffer, a polyol, a surfactant, a chelating agent, and wherein the formulation has a pH at about 5.0 to about 6.0. In some embodiments, the formulation comprises: about 15 mg/mL to about 250 mg/mL of an antibody that specifically binds to an epitope in Kunitz Domain 2 (K2) of Tissue Factor Pathway Inhibitor (TFPI), a buffer, a polyol, a surfactant, a chelating agent, wherein the formulation has a pH at about 5.0 to about 6.0, and wherein the epitope comprises residues Ile105, Arg107, and Leu131, according to the numbering of SEQ ID NO: 2. The formulations described herein have an extended shelf life, preferably of at least about 1 month, about 4 months, about 6 months, about 12 months, about 24 months, about 36 months, about 48 months, or about 60 months (e.g., at about −70° C., at about −20° C., at about 5° C., at about 25° C. or at about 40° C.).

In some embodiments, the formulation comprises at least one TFPI antagonist antibodies (i.e., anti-TFPI antibody). Exemplary TFPI antagonist antibodies include but are not limited to those described in WO 2017/029583, WO 2010/017196, WO 2011/109452, WO 2014/144577, WO 2010/072687, WO 2012/001087, WO 2014/140240, and WO 2015/007880, each of which is herein incorporated by reference in its entirety.

In some embodiments, the TFPI antagonist antibody is selected from the group consisting of TFPI 106 (also known as PF-06741086), TFPI-23, TFPI-107, concizumab (also known as mAb-2021, hz4F36), 2A8 and 2A8-200 (see, for example, US20170073428).

In some embodiments, more than one antibody may be present. At least one, at least two, at least three, at least four, at least five, or more, different antibodies can be present. Generally, the two or more different antibodies have complementary activities that do not adversely affect each other. The antibody or antibodies can also be used in conjunction with other agents that serve to enhance and/or complement the effectiveness of the antibodies.

In some embodiments, the antibody specifically binds to an epitope in Kunitz Domain 2 (K2) of Tissue Factor Pathway Inhibitor (TFPI), wherein the epitope comprises residues Ile105, Arg107, and Leu131, according to the numbering of SEQ ID NO: 2. In some embodiments, the anti-TFPI antibody does not bind to Kunitz Domain 1 (K1) of TFPI. In some embodiments, the epitope further comprises residues Cys106, Gly108, Cys130, Leu131, and Gly132, according to the numbering of SEQ ID NO: 2. In some embodiments, the epitope further comprises Asp102, Arg112, Tyr127, Gly129, Met134, and Glu138, according to the numbering of SEQ ID NO: 2. In some embodiments, the epitope does not comprise: E100, E101, P103, Y109, T111, Y113, F114, N116, Q118, Q121, C122, E123, R124, F125, K126, and L140, according to the numbering of SEQ ID NO: 2. In some embodiments, the epitope does not comprise: D31, D32, P34, C35, K36, E100, E101, P103, Y109, K126, and G128, according to the numbering of SEQ ID NO: 2.

In some embodiments, the antibody comprises a heavy chain variable region (VH) comprising:

(a) a VH complementarity determining region one (CDR-H1) comprising the amino acid sequence of SEQ ID NO: 13, (b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15.

In some embodiments, the antibody comprises a VH comprising an amino acid sequence at least 90%, at least 95%, or at least 99% identical to an amino acid sequence selected from the group consisting of SEQ ID NOs: 16, 18, and 20. In some embodiments, the antibody comprises a VH comprising an amino acid sequence selected from the group consisting of SEQ ID NOs: 16, 18, and 20. In some embodiments, the antibody comprises a VH comprising the amino acid sequence of SEQ ID NO: 16. In some embodiments, the antibody comprises a VH comprising the amino acid sequence of SEQ ID NO: 18. In some embodiments, the antibody comprises a VH comprising the amino acid sequence of SEQ ID NO: 20.

In some embodiments, the antibody comprises a light chain variable region (VL) comprising:

(a) a VL complementarity determining region one (CDR-L1) comprising the amino acid sequence of SEQ ID NO: 8, (b) a VL complementarity determining region two (CDR-L2) comprising the amino acid sequence of SEQ ID NO: 9, and (c) a VL complementarity determining region three (CDR-L3) comprising the amino acid sequence of SEQ ID NO: 10.

In some embodiments, the antibody comprises a VL comprising an amino acid sequence at least 90%, at least 95%, or at least 99% identical to SEQ ID NO: 11. In some embodiments, the antibody comprises a VL comprising the amino acid sequence of SEQ ID NO: 11.

In some embodiments, the antibody comprises a heavy chain comprising the amino acid sequence of SEQ ID NO: 17. In some embodiments, the antibody comprises a heavy chain comprising the amino acid sequence of SEQ ID NO: 19. In some embodiments, the antibody comprises a heavy chain comprising the amino acid sequence of SEQ ID NO: 21. In some embodiments, the antibody comprises a light chain comprising the amino acid sequence of SEQ ID NO: 12.

In some embodiments, the antibody comprises:

(i) a heavy chain variable region (VH) comprising: (a) a CDR-H1 comprising the amino acid sequence of SEQ ID NO: 13, (b) a CDR-H2 comprising the amino acid sequence of SEQ ID NO: 14, and (c) a CDR-H3 comprising the amino acid sequence of SEQ ID NO: 15, and (ii) a light chain variable region (VL) comprising: (a) a CDR-L1 comprising the amino acid sequence of SEQ ID NO: 8, (b) a CDR-L2 comprising the amino acid sequence of SEQ ID NO: 9, and (c) a CDR-L3 comprising the amino acid sequence of SEQ ID NO: 10.

In some embodiments, the antibody comprises a VH comprising the amino acid sequence of SEQ ID NO: 18, and a VL comprising the amino acid sequence of SEQ ID NO:11. In some embodiments, the antibody comprises a heavy chain comprising the amino acid sequence of SEQ ID NO: 19, and comprises a light chain comprising the amino acid sequence of SEQ ID NO: 12.

Exemplary antibodies of the present invention were deposited in the American Type Culture Collection, 10801 University Boulevard, Manassas, Va. 20110-2209, USA, on Jul. 22, 2015. Plasmid vector mAb-TFPI-106 VH having ATCC Accession No. PTA-122329 comprises a DNA insert encoding the heavy chain variable region of antibody TFPI-106, and plasmid vector mAb-TFPI-106 VL having ATCC Accession No. PTA-122328 comprises a DNA insert encoding the light chain variable region of antibody TFPI-106.

In some embodiments, the antibody comprises a VH comprising the amino acid sequence of SEQ ID NO: 16, and a VL comprising the amino acid sequence of SEQ ID NO:11. In some embodiments, the antibody comprises a heavy chain comprising the amino acid sequence of SEQ ID NO: 17, and comprises a light chain comprising the amino acid sequence of SEQ ID NO: 12.

In some embodiments, the antibody comprises a VH comprising the amino acid sequence of SEQ ID NO: 20, and a VL comprising the amino acid sequence of SEQ ID NO:11. In some embodiments, the antibody comprises a heavy chain comprising the amino acid sequence of SEQ ID NO: 21, and comprises a light chain comprising the amino acid sequence of SEQ ID NO: 12.

In some embodiments, the antibody comprises a heavy chain comprising the amino acid sequence of SEQ ID NO: 23, and comprises a light chain comprising the amino acid sequence of SEQ ID NO: 22. In some embodiments, the antibody comprises a heavy chain comprising the amino acid sequence of SEQ ID NO: 25, and comprises a light chain comprising the amino acid sequence of SEQ ID NO: 24.

In some embodiments, the antibody has a serum half-life of at least 25 hours, at least 29 hours, at least 30 hours at least 35 hours, at least 40 hours, at least 50 hours, at least 55 hours, at least 60 hours, at least 65 hours, at least 70 hours, at least 75 hours, at least 80 hours, at least 85 hours, at least 90 hours, at least 95 hours, at least 100 hours, at least 105 hours, at least 110 hours, at least 115 hours, at least 120 hours or at least 125 hours. In some embodiments, the antibody has a serum half-life of at least 25 hours, at least 29 hours, or at least 30 hours. In some embodiments, the antibody has a serum half-life of at least 29 hours. In some embodiments, the antibody has a serum half-life of at least 30 hours. In some embodiments, the antibody has a serum half-life of at least 115 hours, at least 120 hours or at least 125 hours.

In some embodiments, the antibody has a binding affinity ($K_D$) of from about $5\times10^{-7}$ M to about $5\times10^{-11}$ M. In some embodiments, the antibody has a $K_D$ of from about $1\times10^{-8}$ M to about $1\times10^{-10}$ M (0.1 to 10 nm). In some embodiments, the antibody has a $K_D \leq 1$ nM, ≤500 pM, ≤250 pM, ≤200 pM, ≤100 pM, ≤50 pM, ≤20 pM or ≤0 pM. In some embodiments, the antibody does not have a $K_D$ in the low pM range (i.e, ≤100 pM). In some aspects, the $K_D$ is measured by surface plasmon resonance. In some aspects, surface plasmon resonance may be measured using a Biacore. In some aspects, the SPR may be measured using Biacore with captured antibody and solution phase human TFPI.

In some aspects, the antibody's subcutaneous bioavailability may be at least 10% relative to the intravenous bioavailability. In some aspects, the antibody's subcutaneous bioavailability may be at least 15% relative to the intravenous bioavailability. In some aspects, the antibody's subcutaneous bioavailability may be at least 20% relative to the intravenous bioavailability. In some aspects, the antibody's subcutaneous bioavailability may be at least 25% relative to the intravenous bioavailability. In some aspects, the antibody's subcutaneous bioavailability may be at least 27% relative to the intravenous bioavailability. In some aspects, the antibody's subcutaneous bioavailability may be at least 30% relative to the intravenous bioavailability. In some aspects, the antibody's subcutaneous bioavailability may be at least 35% relative to the intravenous bioavailability. In some aspects, the antibody's subcutaneous bioavailability may be at least 40% relative to the intravenous bioavailability. In some aspects, the antibody's subcutaneous bioavailability may be at least 50% relative to the intravenous bioavailability. In some aspects, the antibody's subcutaneous bioavailability may be at least 60% relative to the intravenous bioavailability. In some aspects, the antibody's subcutaneous bioavailability may be at least 70% relative to the intravenous bioavailability. In some aspects, the antibody's subcutaneous bioavailability may be at least 80% relative to the intravenous bioavailability. In some aspects, the antibody's subcutaneous bioavailability may be at least 90% relative to the intravenous bioavailability. In some aspects, the antibody's subcutaneous bioavailability may be at least 99% relative to the intravenous bioavailability.

The antibody may be present in the formulation at a concentration ranging from about 0.1 mg/mL to about 250 mg/mL, from about 15 mg/mL to 250 mg/mL, from about 20 mg/mL to about 175 mg/mL, or from about 25 mg/mL to about 160 mg/mL. For example, in some embodiments, the concentration of antibody is about 0.5 mg/mL, about 1 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 70 mg/mL, about 80 mg/mL, about 90 mg/mL, about 100 mg/mL, about 101 mg/mL, about 102 mg/mL, about 102.5 mg/mL, about 103 mg/mL, about 103.5 mg/mL, about 104 mg/mL, about 104.5 mg/mL, about 105 mg/mL, about 105.5 mg/mL, about 106 mg/mL, about 106.5 mg/mL, about 107 mg/mL, about 107.5 mg/mL, about 108 mg/mL, about 108.5 mg/mL, about 109 mg/mL, about 109.5 mg/mL, about 110 mg/mL, about 111 mg/mL, about 112 mg/mL, about 113 mg/mL, about 114 mg/mL, about 115 mg/mL, about 116 mg/mL, about 117 mg/mL, about 118 mg/mL, about 119 mg/mL, about 120 mg/mL, about 121 mg/mL, about 122 mg/mL, about 123 mg/mL, about 124 mg/mL, about 125 mg/mL, about 126 mg/mL, about 127 mg/mL, about 128 mg/mL, about 129 mg/mL, about 130 mg/mL, about 131 mg/mL, about 132 mg/mL, about 133 mg/mL, about 134 mg/mL, about 135 mg/mL, about 136 mg/mL, about 137 mg/mL, about 138 mg/mL, about 139 mg/mL, about 140 mg/mL, about 141 mg/mL, about 142 mg/mL, about 143 mg/mL, about 144 mg/mL, about 145 mg/mL, about 146 mg/mL, about 147 mg/mL, about 148 mg/mL, about 149 mg/mL, about 150 mg/mL, about 151 mg/mL, about 152 mg/mL, about 153 mg/mL, about 154 mg/mL, about 155 mg/mL, about 156 mg/mL, about 157 mg/mL, about 158 mg/mL, about 159 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, or about 250 mg/mL. In some embodiments, the concentration of antibody in the formulation is about 100 mg/mL, about 115 mg/mL, about 150 mg/mL, or about 158 mg/mL. In some embodiments, the concentration of antibody in the formulation is 150 mg/mL. In some embodiments, the concentration of antibody in the formulation is 155 mg/mL. In some embodiments, the concentration of antibody in the formulation is concentration of antibody in the formulation is 158 mg/mL.

According to the present invention, the buffer (e.g., histidine or succinate buffer) provides the formulation with a pH close to physiological pH for reduced risk of pain or anaphylactoid side effects on injection and provides enhanced antibody stability and resistance to aggregation, oxidation, and fragmentation.

The buffer can be, for example without limitation, acetate, succinate (e.g., disodium succinate hexahydrate), gluconate, citrate, histidine, acetic acid, phosphate, phosphoric acid, ascorbate, tartartic acid, maleic acid, glycine, lactate, lactic acid, ascorbic acid, imidazole, bicarbonate and carbonic acid, succinic acid, sodium benzoate, benzoic acid, gluconate, edetate, acetate, malate, imidazole, tris, phosphate, and mixtures thereof. In some embodiments, the buffer is histidine or succinate. In some embodiments, the succinate buffer comprises disodium succinate hexahydrate (basic form) and/or succinic acid or a mixture thereof. Preferably the buffer is histidine, wherein the histidine buffer comprises L-histidine, L-histidine monohydrochloride (also termed as L-histidine monohydrochloride monohydrate and/or L-histidine hydrochloride monohydrate) or a mixture thereof.

The concentration of the buffer can range from about 0.1 millimolar (mM) to about 100 mM. Preferably, the concentration of the buffer is from about 0.5 mM to about 50 mM, further preferably about 1 mM to about 30 mM, more preferably about 1 mM to about 25 mM. Preferably, the concentration of the buffer is about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. In some embodiments, the buffer is histidine in the concentration of about 20 mM. In some embodiments, the buffer is succinate in the concentration of about 20 mM.

The concentration of the buffer can also range from about 0.01 mg/mL to about 30 mg/mL, from about 0.1 mg/mL to about 5 mg/mL, or from about 0.5 mg/mL to about 4 mg/mL. For example, the concentration of the buffer is about 0.01 mg/mL, 0.02 mg/mL, 0.03 mg/mL, about 0.04 mg/mL, about 0.05 mg/mL, about 0.06 mg/mL, about 0.07 mg/mL, 0.08 mg/mL, 0.09 mg/mL, about 0.10 mg/mL, 0.11 mg/mL, 0.12 mg/mL, 0.13 mg/mL, about 0.14 mg/mL, about 0.15 mg/mL, about 0.16 mg/mL, about 0.17 mg/mL, 0.18 mg/mL, 0.19 mg/mL about 0.20 mg/mL, about 0.25 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 2.0 mg/mL, about 3.0 mg/mL, about 4.0 mg/mL, about 5.0 mg/mL, about 6.0 mg/mL, about 7.0 mg/mL, about 8.0 mg/mL, about 9.0 mg/mL, about 10.0 mg/mL, about 11.0 mg/mL, about 12.0 mg/mL, about 13.0 mg/mL, about 14.0 mg/mL, about 15.0 mg/mL, about 16.0 mg/mL, about 17.0 mg/mL, about 18.0 mg/mL, about 19.0 mg/mL, about 20 mg/mL, about 21.0 mg/mL, about 22.0 mg/mL, about 23.0 mg/mL, about 24.0 mg/mL, about 25.0 mg/mL, about 26.0 mg/mL, about 27.0 mg/mL, about 28.0 mg/mL, about 29.0 mg/mL, or about 30 mg/mL. In some embodiments, the formulation comprises about 0.5-5.0 mg/mL histidine buffer. In some embodiments, the buffer is histidine buffer comprising about 0.1-1.5 mg/mL L-histidine and about 1-3 mg/mL L-histidine monohydrochloride. In some embodiments, the buffer is histidine buffer comprising 1.12 mg/mL L-histidine and 2.67 mg/mL L-histidine monohydrochloride. In some embodiments, the buffer is a succinate buffer comprising about 0.5-5.0 mg/mL disodium succinate hexahydrate and about 0.1-1.0 mg/mL succinic acid. In some embodiments the buffer is a succinate buffer comprising about 4.08 mg/mL disodium succinate hexahydrate and about 0.58 mg/mL succinic acid. In some embodiments the buffer is a succinate buffer comprising about 2.362 mg/mL succinic acid.

In some embodiments, the polyol can have a molecular weight that, for example without limitation, is less than about 600 kD (e.g., in the range from about 120 to about 400 kD), and comprises multiple hydroxyl groups including sugars (e.g., reducing and nonreducing sugars or mixtures thereof, saccharide, or a carbohydrate), sugar alcohols, sugar acids, or a salt or mixtures thereof. Examples of non-reducing sugars include, but are not limited to, sucrose, trehalose, and mixtures thereof. In some embodiments, the polyol is mannitol, trehalose, sorbitol, erythritol, isomalt, lactitol, maltitol, xylitol, glycerol, lactitol, propylene glycol, polyethylene glycol, inositol, or mixtures thereof. In other embodiments, the polyol can be, for example without limitation, a monosaccharide, disaccharide or polysaccharide, or mixtures of any of the foregoing. The saccharide or carbohydrate can be, for example without limitation, fructose, glucose, mannose, sucrose, sorbose, xylose, lactose, maltose, sucrose, dextran, pullulan, dextrin, cyclodextrins, soluble starch, hydroxyethyl starch, water-soluble glucans, or mixtures thereof.

In some embodiments, the polyol is selected from the group consisting of mannitol, trehalose, sorbitol, erythritol, isomalt, lactitol, maltitol, xylitol, glycerol, lactitol, propylene glycol, polyethylene glycol, inositol, fructose, glucose, mannose, sucrose, sorbose, xylose, lactose, maltose, sucrose, dextran, pullulan, dextrin, cyclodextrins, soluble starch, hydroxyethyl starch, water-soluble glucans, or mixtures thereof. In some embodiments, the polyol is sucrose or trehalose. In some embodiments, the polyol is sucrose.

The concentration of the polyol in the formulation ranges from about 1 mg/mL to about 300 mg/mL, from about 1 mg/mL to about 200 mg/mL, or from about 1 mg/mL to about 120 mg/mL. Preferably the concentration of the polyol in the formulation is about 50 mg/mL to about 120 mg/mL, from about 60 mg/mL to about 110 mg/mL, or from about 80 mg/mL to about 90 mg/mL). For example, the concentration of the polyol in the formulation is about 0.5 mg/mL, about 1 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 65 mg/mL, about 70 mg/mL, about 75 mg/mL, about 80 mg/mL, about 81 mg/mL, about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL, about 92 mg/mL, about 93 mg/mL, about 94 mg/mL, about 95 mg/mL, about 96 mg/mL, about 97 mg/mL, about 98 mg/mL, about 99 mg/mL, about 100 mg/mL, about 101 mg/mL, about 102 mg/mL, about 103 mg/mL, about 104 mg/mL, about 105 mg/mL, about 106 mg/mL, about 107 mg/mL, about 108 mg/mL, about 109 mg/mL, about 110 mg/mL, about 111 mg/mL, about 112 mg/mL, about 113 mg/mL, about 114 mg/mL, about 115 mg/mL, about 116 mg/mL, about 117 mg/mL, about 118 mg/mL, about 119 mg/mL, about 120 mg/mL, about 121 mg/mL, about 122 mg/mL, about 123 mg/mL, about 124 mg/mL, about 125 mg/mL, about 126 mg/mL, about 127 mg/mL, about 128 mg/mL, about 129 mg/mL, about 130 mg/mL, about 131 mg/mL, about 132 mg/mL, about 133 mg/mL, about 134 mg/mL, about 135 mg/mL, about 136 mg/mL, about 137 mg/mL, about 138 mg/mL, about 139 mg/mL, about 140 mg/mL, about 141 mg/mL, about 142 mg/mL, about 143 mg/mL, about 144 mg/mL, about 145 mg/mL, about 146 mg/mL, about 147 mg/mL, about 148 mg/mL, about 149 mg/mL, or about 150 mg/mL.

In some embodiments, the polyol is sucrose at a concentration of from about 1 mg/mL to about 300 mg/mL, from about 1 mg/mL to about 200 mg/mL, or from about 1 mg/mL to about 120 mg/m L. Preferably the concentration of the sucrose in the formulation is about 50 mg/mL to about 120 mg/mL, from about 60 mg/mL to about 110 mg/mL, or from about 80 mg/mL to about 90 mg/mL. In some embodiments, the concentration of sucrose in the formulation is about 85 mg/m L. In some embodiments, the concentration of sucrose in the formulation is about 84 mg/mL. In some embodiments, the concentration of sucrose in the formulation is about 90 mg/mL. In some embodiments, the polyol is trehalose at a concentration of about 84 mg/mL or about 85 mg/mL or about 90 mg/mL.

Surfactants, as used in the present invention, can alter the surface tension of a liquid antibody formulation. In certain embodiments, the surfactant reduces the surface tension of a liquid antibody formulation. In still other embodiments, the surfactant can contribute to an improvement in stability of any of the antibody in the formulation. The surfactant can also reduce aggregation of the formulated antibody (e.g., during shipping and storage) and/or minimize the formation of particulates in the formulation and/or reduces adsorption (e.g., adsorption to a container). For example, the surfactant can also improve stability of the antibody during and after a freeze/thaw cycle. The surfactant can be, for example without limitation, a polysorbate, poloxamer, triton, sodium dodecyl sulfate, sodium laurel sulfate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine, myristamidopropyl-dimethylamine, palmidopropyl-dimethylamine, isostearamidopropyl-dimethylamine, sodium methyl cocoyl-taurate, disodium methyl oleyl-taurate, dihydroxypropyl PEG 5 linoleammonium chloride, polyethylene glycol, polypropylene glycol, and mixtures thereof. The surfactant can be, for example without limitation, polysorbate 20, polysorbate 21, polysorbate 40, polysorbate 60, polysorbate 61, polysorbate 65, polysorbate 80, polysorbate 81, polysorbate 85, PEG3350 and mixtures thereof.

The concentration of the surfactant generally ranges from about 0.01 mg/mL to about 10 mg/mL, from about 0.01 mg/mL to about 5.0 mg/mL, from about 0.01 mg/mL to about 2.0 mg/mL, from about 0.01 mg/mL to about 1.5 mg/mL, from about 0.01 mg/mL to about 1.0 mg/mL, from about 0.01 mg/mL to about 0.5 mg/mL, from about 0.01 mg/mL to about 0.4 mg/mL, from about 0.01 mg/mL to about 0.3 mg/mL, from about 0.01 mg/mL to about 0.2 mg/mL, from about 0.01 mg/mL to about 0.15 mg/mL, from about 0.01 mg/mL to about 0.1 mg/mL, from about 0.01 mg/mL to about 0.05 mg/mL, from about 0.1 mg/mL to about 1 mg/mL, from about 0.1 mg/mL to about 0.5 mg/mL, or from about 0.1 mg/mL to about 0.3 mg/mL. Further preferably the concentration of the surfactant is about 0.05 mg/mL, about 0.06 mg/mL, about 0.07 mg/mL, about 0.08 mg/mL, about 0.09 mg/mL, about 0.1 mg/mL, about 0.15 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, or about 1 mg/mL.

In some embodiments, the polysorbate is polysorbate 80 at a concentration ranging from about 0.1 mg/mL to about 0.3 mg/mL, for example, at 0.2 mg/m L.

Chelating agents, as used in the present invention, lower the formation of reduced oxygen species, reduce acidic species (e.g., deamidation) formation, reduce antibody aggregation, and/or reduce antibody fragmentation, and/or reduce antibody oxidation in the formulation of the present invention. For example, the chelating agent can be a multidentate ligand that forms at least one bond (e.g., covalent, ionic, or otherwise) to a metal ion and acts as a stabilizer to complex with species, which might otherwise promote instability.

In some embodiments, the chelating agent can be selected from the group consisting of aminopolycarboxylic acids, hydroxyaminocarboxylic acids, N-substituted glycines, 2-(2-amino-2-oxocthyl) aminoethane sulfonic acid (BES), deferoxamine (DEF), citric acid, niacinamide, and desoxycholates and mixtures thereof. In some embodiments, the chelating agent is selected from the group consisting of ethylenediaminetetraacetic acid (EDTA), diethylenetriamine pentaacetic acid 5 (DTPA), nitrilotriacetic acid (NTA), N-2-acetamido-2-iminodiacetic acid (ADA), bis(aminoethyl) glycolether, N, N, N', N'-tetraacetic acid (EGTA), trans-diaminocyclohexane tetraacetic acid (DCTA), glutamic acid, and aspartic acid, N-hydroxyethyliminodiacetic acid (HIMDA), N,N-bis-hydroxyethylglycine (bicine) and N-(trishydroxymethylmethyl) 10 glycine (tricine), glycylglycine, sodium desoxycholate, ethylenediamine, propylenediamine, diethylenetriamine, triethylenetetraamine (trien), disodium edetate dihydrate (or disodium EDTA dihydrate or EDTA disodium salt), calcium EDTA oxalic acid, malate, citric acid, citric acid monohydrate, and trisodium citrate-dihydrate, 8-hydroxyquinolate, amino acids, histidine, cysteine, methionine, peptides, polypeptides, and proteins and mixtures thereof. In some embodiments, the chelating agent is selected from the group consisting of salts of EDTA including, but not limited to, dipotassium edetate, disodium edetate, edetate calcium disodium, sodium edetate, trisodium edetate, and potassium edetate; and a suitable salt of deferoxamine (DEF) is deferoxamine mesylate (DFM), or mixtures thereof. Chelating agents used in the invention can be present, where possible, as the free acid or free base form or salt form of the compound, also as an anhydrous, solvated or hydrated form of the compound or corresponding salt.

In some embodiments the chelating agent is EDTA. In some embodiments, the chelating agent is a salt of EDTA. In some embodiments, the chelating agent is disodium edetate dihydrate.

The concentration of the chelating agent generally ranges from about 0.01 mg/mL to about 50 mg/mL, from about 0.1 mg/mL to about 10.0 mg/mL, from about 5 mg/mL to about 15.0 mg/mL, from about 0.01 mg/mL to about 1.0 mg/mL, from about 0.02 mg/mL to about 0.5 mg/mL, from about 0.025 mg/mL to about 0.075 mg/mL. Further preferably, the concentration of the chelating agent generally ranges from about 0.01 mM to about 2.0 mM, from about 0.01 mM to about 1.5 mM, from about 0.01 mM to about 0.5 mM, from about 0.01 mM to about 0.4 mM, from about 0.01 mM to about 0.3 mM, from about 0.01 mM to about 0.2 mM, from about 0.01 mM to about 0.15 mM, from about 0.01 mM to about 0.1 mM, from about 0.01 mM to about 0.09 mM, from about 0.01 mM to about 0.08 mM, from about 0.01 mM to about 0.07 mM, from about 0.01 mM to about 0.06 mM, from about 0.01 mM to about 0.05 mM, from about 0.01 mM to about 0.04 mM, from about 0.01 mM to about 0.03 mM, from about 0.01 mM to about 0.02 mM, from about 0.02, or from about 0.05 mM to about 0.01 mM. Preferably the concentration of the chelating agent can be about 0.01 mg/mL, about 0.02 mg/mL, about 0.025 mg/mL, about 0.03 mg/mL, about 0.04 mg/mL, about 0.05 mg/mL, about 0.06 mg/mL, about 0.07 mg/mL, about 0.075 mg/mL, about 0.08 mg/mL, about 0.09 mg/mL, about 0.10 mg/mL, or about 0.20 mg/mL. Further preferably the concentration of chelating agent is about 0.025 mg/mL, about 0.03 mg/mL, about 0.035 mg/mL, about 0.04 mg/mL, about 0.045 mg/mL, about 0.05 mg/mL, about 0.055 mg/mL, about 0.06 mg/mL, about 0.065 mg/mL, about 0.07 mg/mL, or about 0.075 mg/mL. Most preferably, the concentration of the chelating agent is about 0.05 mg/mL.

In some embodiments, the chelating agent is disodium edetate dihydrate in a concentration of about 0.05 mg/mL. In some embodiments, the chelating agent is ethylenediaminetetraacetic acid (EDTA) in a concentration of about 0.05 mg/mL.

In some embodiments, the pH can be in the range of about pH 5.0 to about 6.6, preferably between about pH 5.0 to 6.5 or about 5.0 to 6.0, and most preferably between pH 5.2 to 5.8. In some embodiments, the pH for the formulation of the present invention can be in the range selected from between any one of about pH 5.2, 5.3, 5.4, 5.5, or 5.6 and any one of about pH 6.5, 6.4, 6.3, 6.2, 6.1, 6.0, 5.9, 5.8 or 5.7. In some embodiments the pH can be selected from pH values of any of about pH 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4 or 7.5. In some embodiments, the pH is pH 5.8+/−0.5, and in some embodiments, the pH is pH 5.8+/−0.3.

In some embodiments the formulation can comprise a preservative. Preferably the preservative agent is selected from phenol, m-cresol, benzyl alcohol, benzalkonium chloride, benzalthonium chloride, phenoxyethanol and methyl paraben.

The concentration of the preservative generally ranges from about 0.001 mg/mL to about 50 mg/mL, from about 0.005 mg/mL to about 15.0 mg/mL, from about 0.008 mg/mL to about 12.0 mg/mL or from about 0.01 mg/mL to about 10.0 mg/mL. Preferably the concentration of preservative can be about 0.1 mg/mL, 0.2 mg/mL, 0.3 mg/mL, about 0.4 mg/mL, about 0.5 mg/mL, about 0.6 mg/mL, about 0.7 mg/mL, 0.8 mg/mL, 0.9 mg/mL about 1.0 mg/mL, 2.0 mg/mL, 3.0 mg/mL, about 4.0 mg/mL, about 5.0 mg/mL, about 6.0 mg/mL, about 7.0 mg/mL, 8.0 mg/mL, 9.0 mg/mL about 9.1 mg/mL, about 9.2 mg/mL, 9.3 mg/mL, 9.4 mg/mL, 9.5 mg/mL, 9.6 mg/mL, 9.7 mg/mL, 9.8 mg/mL, 9.9 mg/mL, 10.0 mg/mL. Most preferably, the concentration of preservative is about 0.1 mg/mL or 9.0 mg/mL.

In some embodiments, the formulation does not contain a preservative.

In some embodiments, the antibody can be selected from the group consisting of monoclonal antibodies, polyclonal antibodies, antibody fragments (e.g., Fab, Fab', F(ab')2, Fv, Fc, ScFv etc.), chimeric antibodies, bispecific antibodies, heteroconjugate antibodies, single chain (ScFv), mutants thereof, fusion proteins comprising an antibody portion (e.g., a domain antibody), humanized antibodies, human antibodies, and any other modified configuration of the immunoglobulin molecule that comprises an antigen recognition site of the required specificity, including glycosylation variants of antibodies, amino acid sequence variants of antibodies, and covalently modified antibodies. The antibody may be murine, rat, human, or any other origin (including chimeric or humanized antibodies). In some embodiments, the antibody is human. Preferably the antibody is isolated, further preferably it is substantially pure. Where the antibody is an antibody fragment this preferably retains the functional characteristics of the original antibody i.e. the ligand binding and/or antagonist or agonist activity.

In some embodiments, the antibody heavy chain constant region may be from any type of constant region, such as IgG, IgM, IgD, IgA, and IgE; and any isotypes, such as IgG1, IgG2, IgG3, and IgG4. Preferably the antibody is an IgG1 antibody.

According to a further aspect of the present invention there is provided a formulation comprising or consisting of: about 15 mg/mL to about 250 mg/mL of a Tissue Factor Pathway Inhibitor (TFPI) antibody; about 1 mM to about 100 mM of a buffer; about 1 mg/mL to about 300 mg/mL of a polyol; about 0.01 mg/mL to about 10 mg/mL of a surfactant; about 0.01 mg/mL to about 50.0 mg/mL of a chelating agent; and wherein the formulation has a pH at about 5.0 to about 6.0. In some embodiments, the antibody comprises (i) a heavy chain variable region (VH) comprising: (a) a VH complementarity determining region one (CDR-H1) comprising the amino acid sequence of SEQ ID NO: 13; (b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15, and (ii) a light chain variable region (VL) comprising: (a) a VL complementarity determining region one (CDR-L1) comprising the amino acid sequence of SEQ ID NO: 8; (b) a VL complementarity determining region two (CDR-L2) comprising the amino acid sequence of SEQ ID NO: 9; and (c) a VL complementarity determining region three (CDR-L3) comprising the amino acid sequence of SEQ ID NO: 10. In some embodiments, the anti-TFPI antibody comprises a VH region comprising the amino acid sequence of SEQ ID NO: 18, and a VL region comprising the amino acid sequence of SEQ ID NO: 11. In some embodiments, the anti-TFPI antibody is TFPI-106 (also known as PF-06741086 or marstacimab). In some embodiments, the buffer is histidine buffer, the polyol is sucrose or trehalose, the surfactant is a polysorbate (e.g., polysorbate 80), and/or the chelating agent is EDTA or disodium edetate dihydrate. In some embodiments, the buffer is histidine buffer, the polyol is sucrose, the surfactant is polysorbate 80, and the chelating agent is disodium edetate dihydrate.

In some embodiments, the formulation of an anti-TFPI antibody drug substance disclosed herein may be stored in sterilized ethylene vinyl acetate (EVA) bags with ethylene vinyl acetate monomaterial (EVAM) product contact surface. In some embodiments, the formulation of an anti-TFPI antibody drug substance disclosed herein may be stored in sterilized high density polyethylene bottles (HDPE). In some embodiments, the formulation of an anti-TFPI antibody drug substance disclosed herein may be stored in a stainless steel container. In some embodiments, the formulation of an anti-TFPI antibody drug product disclosed herein may be stored in a sterilized vial or pre-filled syringe (PFS). In some embodiments, the formulation of an anti-TFPI antibody drug product disclosed herein may be stored in a pre-filled pen (PFP).

According to a further aspect of the present invention, there is provided a formulation comprising or consisting of: about 100 mg/mL, about 110 mg/mL, about 115 mg/mL, about 120 mg/mL, about 130 mg/mL, about 140 mg/mL, about 150 mg/mL, about 158 mg/mL, about 160 mg/mL, or about 200 mg/mL of a Tissue Factor Pathway Inhibitor antibody (e.g., human anti-TFPI antibody); about 1 mM to about 100 mM of a buffer; about 1 mg/mL to about 300 mg/mL of a polyol; about 0.01 mg/mL to about 10 mg/mL of a surfactant; about 0.01 mg/mL to about 1.0 mg/mL of a chelating agent; and wherein the formulation has a pH at about 5.0 to about 6.0. In some embodiments, the antibody comprises (i) a heavy chain variable region (VH) comprising: (a) a VH complementarity determining region one (CDR-H1) comprising the amino acid sequence of SEQ ID NO: 13; (b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15, and (ii) a light chain variable region (VL) comprising: (a) a VL complementarity determining region one (CDR-L1) comprising the amino acid sequence of SEQ ID NO: 8; (b) a VL complementarity determining region two (CDR-L2) comprising the amino acid sequence of SEQ ID NO: 9; and (c) a VL complementarity determining region three (CDR-L3) comprising the amino acid sequence of SEQ ID NO: 10. In some embodiments, the anti-TFPI antibody is TFPI-106 (also known as PF-06741086 or marstacimab).

According to a further aspect of the present invention there is provided a formulation comprising or consisting of:

about 50 mg/mL to about 160 mg/mL of a Tissue Factor Pathway Inhibitor antibody (e.g., human anti-TFPI antibody); about 20 mM of a buffer; about 1 mg/mL to about 120 mg/mL of a polyol; about 0.1 mg/mL to about 0.3 mg/mL of a surfactant; about 0.025 mg/mL to about 0.075 mg/mL of a chelating agent; and wherein the formulation has a pH at about 5.0 to about 6.0. In some embodiments, the antibody comprises (i) a heavy chain variable region (VH) comprising: (a) a VH complementarity determining region one (CDR-H1) comprising the amino acid sequence of SEQ ID NO: 13; (b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15, and (ii) a light chain variable region (VL) comprising: (a) a VL complementarity determining region one (CDR-L1) comprising the amino acid sequence of SEQ ID NO: 8; (b) a VL complementarity determining region two (CDR-L2) comprising the amino acid sequence of SEQ ID NO: 9; and (c) a VL complementarity determining region three (CDR-L3) comprising the amino acid sequence of SEQ ID NO: 10. In some embodiments, the anti-TFPI antibody comprises a VH region comprising the amino acid sequence of SEQ ID NO: 18, and a VL region comprising the amino acid sequence of SEQ ID NO: 11. In some embodiments, the anti-TFPI antibody is TFPI-106 (also known as PF-06741086 or marstacimab). In some embodiments, the buffer is a histidine buffer, the polyol is sucrose, the chelating agent is disodium edetate dihydrate, and/or the surfactant is polysorbate 80. In some embodiments, the concentration of the antibody is 100 mg/mL, 115 mg/mL, 150 mg/mL or 158 mg/mL.

In some embodiments, provided is an aqueous formulation comprising or consisting of: about 150 mg/mL of a Tissue Factor Pathway Inhibitor antibody (e.g., human anti-TFPI antibody); about 20 mM of histidine buffer; about 85 mg/mL of sucrose; about 0.2 mg/mL of polysorbate 80; about 0.05 mg/mL of disodium edetate dihydrate; and wherein the formulation has a pH at about 5.8. In some embodiment, the antibody comprises (i) a heavy chain variable region (VH) comprising: (a) a VH complementarity determining region one (CDR-H1) comprising the amino acid sequence of SEQ ID NO: 13; (b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15, and (ii) a light chain variable region (VL) comprising: (a) a VL complementarity determining region one (CDR-L1) comprising the amino acid sequence of SEQ ID NO: 8; (b) a VL complementarity determining region two (CDR-L2) comprising the amino acid sequence of SEQ ID NO: 9; and (c) a VL complementarity determining region three (CDR-L3) comprising the amino acid sequence of SEQ ID NO: 10. In some embodiments, the anti-TFPI antibody comprises a VH region comprising the amino acid sequence of SEQ ID NO: 18, and a VL region comprising the amino acid sequence of SEQ ID NO: 11. In some embodiments, the anti-TFPI antibody comprises a heavy chain comprising the amino acid sequence of SEQ ID NO: 19, and a light chain comprising the amino acid sequence of SEQ ID NO: 12. In some embodiments, the anti-TFPI antibody is TFPI-106 (also known as PF-06741086 or marstacimab).

In some embodiments, the formulation as described herein has a shelf life of at least or more than about 1 month, about 3 months, about 6 months, about 12 months, about 18 months, about 24 months, about 30 months, about 36 months, about 42 months, about 48 months or about 60 months (e.g., at −20° C., at 5° C., 25° C., or 40° C.). For example, in some embodiments, the formulation of the present invention has a shelf life of at least about 1 month, about 3 months, about 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months, or 60 months (e.g., at −20° C., at 5° C., 25° C., or 40° C.). In some embodiments, the formulation described herein has a shelf life of at least about 24 months at 5±3° C.

In some embodiments, the formulation as described herein has less than about 7% HMMS at 40° C./75% RH for up to 1 month, 2 months, 3 months, 4 months, 5 months, or 6 months (e.g., as measured by size exclusion HPLC). In some embodiments, the formulation as described herein has less than about 3% HMMS at 40° C. for up to 1 month, 2 months, or 3 months (e.g., as measured by size exclusion HPLC). In some embodiments, the formulation as described herein has less than about 2% HMMS at 40° C. for up to 1 month (e.g., as measured by size exclusion HPLC).

In some embodiments, the formulation as described herein has less than about 2% HMMS at 5±3° C. for up to 24 months (e.g., as measured by size exclusion HPLC). In some embodiments, the formulation as described herein has less than about 1% HMMS at 5±3° C. for up to 1 month, 2 months, 3 months, 4 months, 5 months, 6 months, 12 months, 18 months or 24 months (e.g., as measured by size exclusion HPLC). In some embodiments, the formulation as described herein has less than about 2% Fragment at 5±3° C. for up to 24 months (e.g., as measured by reducing capillary gel electrophoresis).

Unless stated otherwise, the concentrations listed herein are those concentrations at ambient conditions, i.e., at 25° C. and atmospheric pressure.

Methods of Using the Anti-TFPI Antibody Formulation

The formulations described herein are useful in various applications including, but are not limited to, therapeutic treatment methods. A therapeutic method comprises administering the formulation of the invention to a subject in need thereof.

Exemplary therapeutic uses of the formulation of the invention include shortening bleeding time in a subject in need thereof, treating or preventing deficiencies in blood coagulation or a blood disorder (e.g., hemophilia A, hemophilia B, hemophilia C, von Willebrand Disease (vWD), Factor VII deficiency, Factor VIII, Factor IX, or Factor XI deficiency), treating or preventing thrombocytopenia, and treating or preventing platelet disorders (disorders of platelet function or number). The formulations described herein may also be used for treating uncontrolled bleeding (for example, uncontrolled bleeding in indications such as trauma and hemorrhagic stroke). The formulations described herein may also be used in prophylactic treatment (e.g., to treat or prevent bleeding before surgeries).

In particular, the formulations described herein can be used to treat deficiencies or defects in coagulation or disorders of coagulation. For example, the formulations described herein may be used to reduce or inhibit the interaction of TFPI with FXa, or to reduce TFPI-dependent inhibition of the TF/FVIIa/FXa activity.

Accordingly, in some embodiments, the subject suffers from or is susceptible to a deficiency in blood coagulation or a blood disorder such as the following: In some embodiments, the subject suffers from or is susceptible to hemophilia A, B or C. In some embodiments, the subject suffers from or is susceptible to hemophilia A or B. In some embodiments, the subject suffers from or is susceptible to hemophilia A and has neutralizing antibodies (i.e., inhibitors) against coagulation Factor VIII. In some embodiments, the subject suffers from or is susceptible to hemophilia B and has neutralizing antibodies (i.e., inhibitors) against coagulation Factor IX. In some embodiments, the subject suffers from or is susceptible to hemophilia C and has neutralizing antibodies (i.e., inhibitors) against coagulation Factor XI. In some embodiments, the subject suffers from or is susceptible to von Willebrand Disease (vWD). In some embodiments, the subject suffers from or is susceptible to a platelet disorder. In some embodiments, the subject suffers from or is susceptible to a factor VII deficiency. In some embodiments, the subject suffers from or is susceptible to a factor XI deficiency.

Formulations comprising TFPI antagonist antibodies or antigen-binding portions described herein may be used in combination with a clotting agent. The present invention provides for the separate, simultaneous or sequential administration of the formulations of the invention with a clotting agent. In some embodiments, the formulations described herein further comprise a clotting agent. Examples of clotting agent include, but are not limited to, Factor Vila, Factor VIII, Factor IX, tranexamic acid and bypass agents (e.g., anti-inhibitor coagulant complex or FEIBA).

In some embodiments, provided is a use of the formulation of the present invention for the manufacture of a medicament for shortening bleeding time.

In some embodiments, the formulation of the present invention can be administered directly into the blood stream, into muscle, into tissue, into fat, or into an internal organ of a subject. Suitable means for parenteral administration include intravenous, intraocular, intravitreal, intraarterial, intraperitoneal, intrathecal, intraventricular, intraurethral, intrasternal, intracranial, intramuscular, intra-ossial, intradermal and subcutaneous. Suitable devices for parenteral administration include needle (including microneedle, microprojections, soluble needles and other micropore formation techniques) injectors, needle-free injectors and infusion techniques. In some embodiments, the formulation of the present invention is administered to the subject intravenously or subcutaneously. In some embodiments, the formulation of the present invention is administered to the subject subcutaneously. In some embodiments, the formulation of the present invention is administered to the subject intravenously.

In some embodiments, the administration pattern of the formulation of the present invention comprises administration of a dose of the formulation once every week, once every two weeks, once every three weeks, once every four weeks, once every five weeks, once every six weeks, once every seven weeks, once every eight weeks, once every nine weeks, once every ten weeks, once every fifteen weeks, once every twenty weeks, once every twenty five weeks, or once every twenty six weeks. In some embodiments, the formulation described herein is administered once every month, once every two months, once every three months, once every four months, once every five months, or once every six months. In some embodiments, the formulation described herein in administered daily or weekly (i.e., once a week). The progress of this therapy is easily monitored by conventional techniques and assays. The dosing regimen can vary over time.

In some embodiments, the formulation described herein is administered at an initial antibody dose of about 300 mg followed by subsequent weekly (i.e., once a week) doses of about 150 mg. In some embodiments, the formulation described herein is administered weekly (i.e., once a week) at an antibody dose of about 150 mg. In some embodiments, the formulation described herein is administered weekly (i.e., once a week) at an antibody dose of about 300 mg. In some embodiments, the formulation described herein is administered weekly (i.e., once a week) at an antibody dose of about 450 mg.

For the purpose of the present invention, the appropriate dosage of the medicament will depend on the antibody employed, the type and severity of the disorder to be treated, whether the agent is administered for preventative or therapeutic purposes, previous therapy, the patient's clinical history and response to the agent, and the discretion of the attending physician. Typically, the clinician will administer the medicament, until a dosage is reached that achieves the desired result. Dosages may be determined empirically.

The following examples are offered for illustrative purposes only and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1. Stability Studies of Anti-TFPI Antibody

This example illustrates the stability of a formulation containing anti-TFPI antibody in high density polyethylene (HDPE) bottles, vials, and prefilled syringes.

Anti-TFPI antibody at 100 mg/mL, 115 mg/mL, and 150 mg/mL was prepared in 20 mM histidine, 85 mg/mL sucrose, 0.05 mg/mL edetate disodium dihydrate, 0.2 mg/mL polysorbate 80 at pH 5.8. In this example, the anti-TFPI antibody used has a heavy chain variable region having the amino acid sequence of SEQ ID NO:18, and a light chain variable region having the amino acid sequence of SEQ ID NO:11.

Anti-TFPI antibody at 115 mg/mL was filled into HDPE bottles and stored at −20±5° C. and 5±3° C. for a duration of at least 3 months (i.e., 12 weeks).

Anti-TFPI antibody at 100 mg/mL and 150 mg/mL was filled into Type I glass vials, sealed with coated stoppers, capped with aluminum seals and stored in the inverted orientation at 5±3° C., 25° C./60% relative humidity (RH), and 40° C./75% relative humidity (RH) for a duration of at least 3 months (i.e., 12 weeks). In addition, anti-TFPI antibody at 150 mg/mL was also filled into 2.25 mL and 1 mL Type I glass prefilled syringes (PFS), stoppered with a coated plunger stopper and stored in the horizontal orientation at 5±3° C., 25° C./60% RH, and 40° C./75% RH for a duration of at least 3 months (i.e., 12 weeks).

Samples were then analyzed for quality attributes that are routinely used to monitor protein degradation. For example, the analysis consisted of size exclusion high performance liquid chromatography (SE-HPLC) to assess high molecular mass species (HMMS), reducing and non-reducing Capillary Gel Electrophoresis (CGE) to assess purity and fragmentation, and imaged capillary isoelectric focusing (iCE) to assess charge heterogeneity such as acidic, basic, and main species. Analysis also included evaluating the relative potency of anti-TFPI antibody using an inhibition assay.

Specific analytical procedures, including compendial and non-compendial methods, were used to assess the characteristics, purity, and relative potency of the anti-TFPI antibody. Descriptions of the analytical procedures are provided below. Results are summarized in Tables 1-8.

Appearance (Clarity and Coloration): The drug substance is assessed for clarity and coloration in accordance with the current European Pharmacopoeia procedure, Ph. Eur. 2.2.1 and Ph. Eur. 2.2.2, respectively.

The drug substance is analyzed for pH in accordance with the current USP Procedure <791>.

Protein Concentration by UV: Using a spectrophotometer, the absorbance at 280 nm is used to determine the concentration of the test sample. The specific absorption coefficient or absorptivity (a280) for PF-06741086 (given below) is used for the concentration calculation. a280=1.45 mL mg-1 cm-1

Imaged Capillary Isoelectric Focusing (iCE): The Imaged capillary isoelectric focusing (iCE) method is used to evaluate charge heterogeneity. iCE separates protein species based on their charge differences in a pH gradient generated by ampholytes under the influence of an electric field and is used to monitor product charge heterogeneity. Protein charge species are focused within a capillary under DC voltage and detected at 280 nm with whole capillary imaging.

Size Exclusion HPLC (SE-HPLC): The SE-HPLC method is used to determine product purity. The test samples are diluted and injected onto a size-exclusion column. The content of high molecular mass species (HMMS) and monomer is reported as the percent of the total area for all protein-related peaks.

Capillary Gel Electrophoresis (CGE) Reducing: This method is used to determine the purity of the reduced protein. Samples are denatured with SDS and heated in the presence of a reducing agent. The protein is reduced into heavy and light chains which are electrophoretically separated in a capillary containing sieving medium and detected using UV spectroscopy. The separation allows quantitation of the resolved heavy and light chains as well as size related impurities. The purity is reported as the total percent of heavy and light chains.

Capillary Gel Electrophoresis (CGE) Non-Reducing: This method is used to determine the purity of the intact protein. Samples are denatured with SDS and heated in the presence of an alkylating agent. The protein is electrophoretically separated in a capillary containing sieving medium and detected using UV spectroscopy. The separation allows quantitation of the resolved intact IgG as well as size related impurities. The purity is reported as the percent of IgG.

Lysyl Endotoproteinase (Lys-C) Mapping: This method is used to determine the percent oxidation in the anti-TFPI antibody localized at a Fc-peptide containing a methionine residue. Samples of anti-TFPI antibody are digested into peptide fragments using lysyl endoproteinase (Lys-C). The resulting peptide fragments are separated by reversed-phase HPLC. The separation of the Fc-peptide and oxidized Fc-peptide allow for the percent oxidation to be determined and monitored for the anti-TFPI antibody.

Biological Activity by Inhibition Assay: The inhibition assay method is used to evaluate the in vitro biological activity of PF-06741086. The inhibition assay demonstrates that PF-06741086 is capable of inhibiting the TFPI:FXa complex formation, resulting in an increase of free human coagulation factor Xa (FXa) which in turn results in free FXa available for coagulation activity.

TFPI is added to a microtiter plate. Dilutions of PF-06741086 reference material and test samples are added to the microtiter plate to allow binding of the antibody to its target. FXa is then added to the microtiter plate and binds the available TFPI, not bound by PF-06741086 and forming a TFPI: FXa complex. Free FXa is detected using a chromogenic substrate Spectrozyme FXa. After substrate addition, the colorimetric response is measured spectrophotometrically.

The method of data analysis includes non-linear curve fitting and an assessment of parallelism between the standard and sample curves. Sample potency is determined from the shift in IC50 between the parallel curves. The specific activity of a sample, expressed in units per PF-06741086, is computed by multiplying the relative potency value by the number of units assigned to one milligram (mg) of the reference material.

TABLE 1

SE-HPLC results for high molecular mass species (% HMMS)

| Configuration | Storage Temperature | HMMS (%) 0 months | 1 month | 3 months | 6 months | 12 months | 18 months | 24 months |
|---|---|---|---|---|---|---|---|---|
| 115 mg/mL, HDPE bottle | −20 ± 5° C. | NMT 0.5 | NMT 0.5 | NMT 0.5 | NS | NMT 0.5 | NMT 0.5 | 0.3 |
| 115 mg/mL, HDPE bottle | 5 ± 3° C. | NMT 0.5 | NMT 0.5 | 0.5 | NS | NS | NS | NS |
| 150 mg/mL, Vial | | 0.6 | 0.7 | 0.7 | 0.7 | 0.8 | NS | 0.9 |
| 150 mg/mL, 2.25 mL PFS | | 0.5 | 0.5 | 0.5 | 0.7 | 0.7 | 0.4 | 0.7 |
| 150 mg/mL, 1 mL PFS | | 0.5 | 0.5 | 0.5 | 0.7 | 0.6 | 0.4 | 0.7 |
| 150 mg/mL, Vial | 25° C./60% RH | 0.6 | 0.8 | 0.9 | 1.1 | 1.4 | NS | 2.2 |
| 150 mg/mL, 2.25 mL PFS | | 0.5 | 0.6 | 0.7 | 1.0 | 1.1 | NS | NS |
| 150 mg/mL, 1 mL PFS | | 0.5 | 0.7 | 0.7 | 1.0 | 1.2 | NS | NS |
| 100 mg/mL, Vial | 40° C./75% RH | 0.5 | 1.1 | 1.5 | NS | NS | NS | NS |
| 150 mg/mL, Vial | | 0.6 | 1.2 | 2.1 | 5.2 | 15.8 | NS | NS |

TABLE 1-continued

SE-HPLC results for high molecular mass species (% HMMS)

| Configuration | Storage Temperature | HMMS (%) 0 months | 1 month | 3 months | 6 months | 12 months | 18 months | 24 months |
|---|---|---|---|---|---|---|---|---|
| 150 mg/mL, 2.25 mL PFS | | 0.5 | 0.9 | 2.1 | 4.4 | NS | NS | NS |
| 150 mg/mL, 1 mL PFS | | 0.5 | 1.0 | 2.4 | 6.3 | NS | NS | NS |

NMT = Not More Than
NS = Not scheduled

TABLE 2

CGE (reducing) results for Heavy Chain + Light Chain (%)

| Configuration | Storage Temperature | Heavy Chain + Light Chain (%) 0 months | 1 month | 3 months | 6 months | 12 months | 18 months | 24 months |
|---|---|---|---|---|---|---|---|---|
| 115 mg/mL, HDPE bottle | −20 ± 5° C. | 98.5 | 98.2 | 98.6 | 98.6 | 98.6 | 98.4 | 98.5 |
| 115 mg/mL, HDPE bottle | 5 ± 3° C. | 98.5 | 98.5 | 98.7 | 98.5 | NS | NS | NS |
| 150 mg/mL, Vial | | 97.9 | 98.0 | 97.6 | 97.4 | 98.7 | NS | 97.4 |
| 150 mg/mL, 2.25 mL PFS | | 97.4 | 97.2 | 97.4 | 97.2 | 97.1 | 97.3 | 97.2 |
| 150 mg/mL, 1 mL PFS | | 97.6 | 96.8 | 97.7 | 97.7 | 97.1 | 97.2 | 97.3 |
| 150 mg/mL, Vial | 25° C./60% RH | 97.9 | 97.9 | 96.9 | 96.9 | 96.0 | NS | 92.7 |
| 150 mg/mL, 2.25 mL PFS | | 97.4 | 97.2 | 96.4 | 96.1 | 95.2 | NS | NS |
| 150 mg/mL, 1 mL PFS | | 97.6 | 97.2 | 96.4 | 96.2 | 94.6 | NS | NS |
| 100 mg/mL, Vial | 40° C./75% RH | 98.3 | 97.5 | 94.1 | NS | NS | NS | NS |
| 150 mg/mL, Vial | | 97.9 | 97.6 | 93.8 | 89.9 | 76.4 | NS | NS |
| 150 mg/mL, 2.25 mL PFS | | 97.4 | 96.0 | 93.2 | 89.5 | NS | NS | NS |
| 150 mg/mL, 1 mL PFS | | 97.6 | 96.2 | 92.9 | 89.2 | NS | NS | NS |

NS = Not Scheduled

TABLE 3

CGE (reducing) results for Fragment (%)

| Configuration | Storage Temperature | Fragment (%) 0 months | 1 month | 3 months | 6 months | 12 months | 18 months | 24 months |
|---|---|---|---|---|---|---|---|---|
| 115 mg/mL, HDPE bottle | −20 ± 5° C. | NMT 0.3 | NMT 0.3 | NMT 0.3 | NMT 0.3 | NMT 0.3 | NMT 0.3 | NMT 0.3 |
| 115 mg/mL, HDPE bottle | 5 ± 3° C. | NMT 0.3 | NMT 0.3 | NMT 0.3 | NMT 0.3 | NS | NS | NS |
| 150 mg/mL, Vial | | 0.4 | NMT 0.3 | 0.6 | 0.8 | 0.3 | NS | 0.8 |
| 150 mg/mL, 2.25 mL PFS | | NMT 0.3 | 0.7 | 0.4 | 0.7 | 1.2 | 0.9 | 0.8 |
| 150 mg/mL, 1 mL PFS | | NMT 0.3 | 1.1 | 0.3 | 0.5 | 1.1 | 1.0 | 0.8 |
| 150 mg/mL, Vial | 25° C./60% RH | 0.4 | NMT 0.3 | 0.9 | 1.3 | 1.9 | NS | 5.4 |
| 150 mg/mL, 2.25 mL PFS | | NMT 0.3 | 0.8 | 1.0 | 1.9 | 3.1 | NS | NS |
| 150 mg/mL, 1 mL PFS | | NMT 0.3 | 0.9 | 1.1 | 1.8 | 3.4 | NS | NS |
| 100 mg/mL, Vial | 40° C./75% RH | <0.3 | 1.0 | 4.2 | NS | NS | NS | NS |
| 150 mg/mL, Vial | | 0.4 | 0.6 | 3.8 | 7.6 | 19.3 | NS | NS |
| 150 mg/mL, 2.25 mL PFS | | NMT 0.3 | 1.8 | 4.3 | 8.0 | NS | NS | NS |

TABLE 3-continued

CGE (reducing) results for Fragment (%)

| Configuration | Storage Temperature | Fragment (%) 0 months | 1 month | 3 months | 6 months | 12 months | 18 months | 24 months |
|---|---|---|---|---|---|---|---|---|
| 150 mg/mL, 1 mL PFS | | NMT 0.3 | 1.6 | 4.6 | 8.0 | NS | NS | NS |

NMT = Not More Than
NS = Not Scheduled

TABLE 4

CGE (non-reducing) results for Intact IgG (%)

| Configuration | Storage Temperature | Intact IgG (%) 0 months | 1 month | 3 months | 6 months | 12 months | 18 months | 24 months |
|---|---|---|---|---|---|---|---|---|
| 115 mg/mL, HDPE bottle | −20 ± 5° C. | 96.0 | NS | NS | NS | NS | NS | 95.8 |
| 115 mg/mL, HDPE bottle | 5 ± 3° C. | NS | NS | NS | NS | NS | NS | NS |
| 150 mg/mL, Vial | | 97.0 | 97.9 | 97.9 | 97.7 | 97.3 | NS | 97.9 |
| 150 mg/mL, 2.25 mL PFS | | 97.5 | 98.1 | 97.0 | 97.9 | 97.5 | 97.6 | 98.1 |
| 150 mg/mL, 1 mL PFS | | 97.4 | 97.8 | 97.2 | 97.8 | 97.4 | 97.7 | 97.8 |
| 150 mg/mL, Vial | 25° C./60% RH | 97.0 | 96.9 | 96.9 | 95.7 | 91.9 | NS | 90.3 |
| 150 mg/mL, 2.25 mL PFS | | 97.5 | 97.7 | 96.0 | 95.8 | 93.0 | NS | NS |
| 150 mg/mL, 1 mL PFS | | 97.4 | 97.4 | 95.8 | 95.5 | 92.3 | NS | NS |
| 100 mg/mL, Vial | 40° C./75% RH | NS | NS | NS | NS | NS | NS | NS |
| 150 mg/mL, Vial | | 97.0 | 94.8 | 89.6 | 81.1 | 60.1 | NS | NS |
| 150 mg/mL, 2.25 mL PFS | | 97.5 | 95.6 | 89.1 | 83.2 | NS | NS | NS |
| 150 mg/mL, 1 mL PFS | | 97.4 | 95.3 | 87.9 | 80.7 | NS | NS | NS |

NS = Not Scheduled

TABLE 5 iCE results for Acidic (%)

| Configuration | Storage Temperature | Acidic (%) 0 months | 1 month | 3 months | 6 months | 12 months | 18 months | 24 months |
|---|---|---|---|---|---|---|---|---|
| 115 mg/mL, HDPE bottle | −20 ± 5° C. | 19.8 | 23.7 | 19.3 | 20.0 | 19.8 | 19.7 | 18.9 |
| 115 mg/mL, HDPE bottle | 5 ± 3° C. | 19.8 | 22.9 | 20.3 | 21.4 | NS | NS | NS |
| 150 mg/mL, Vial | | 22.7 | 21.2 | 24.6 | 23.2 | 21.2 | NS | 22.3 |
| 150 mg/mL, 2.25 mL PFS | | 22.3 | 23.2 | 22.9 | 22.5 | 24.4 | 22.7 | 22.9 |
| 150 mg/mL, 1 mL PFS | | 21.3 | 22.4 | 24.5 | 22.2 | 24.2 | 22.3 | 23.0 |
| 150 mg/mL, Vial | 25° C./60% RH | 22.7 | 23.3 | 29.7 | 34.3 | 42.9 | NS | 59.1 |
| 150 mg/mL, 2.25 mL PFS | | 22.3 | 25.3 | 28.5 | 34.5 | 43.8 | NS | NS |
| 150 mg/mL, 1 mL PFS | | 21.3 | 24.6 | 28.9 | 33.9 | 45.0 | NS | NS |
| 100 mg/mL, Vial | 40° C./75% RH | 18.5 | 34.9 | 58.2 | NS | NS | NS | NS |
| 150 mg/mL, Vial | | 22.7 | 38.0 | 64.6 | 82.4 | 96.0 | NS | NS |
| 150 mg/mL, 2.25 mL PFS | | 22.3 | 40.4 | 62.0 | 80.8 | NS | NS | NS |
| 150 mg/mL, 1 mL PFS | | 21.3 | 39.9 | 62.4 | 84.1 | NS | NS | NS |

NS = Not Scheduled

TABLE 6

| iCE results for Basic (%) | | | | | | | | |
|---|---|---|---|---|---|---|---|---|
| | | Basic (%) | | | | | | |
| Configuration | Storage Temperature | 0 months | 1 month | 3 months | 6 months | 12 months | 18 months | 24 months |
| 115 mg/mL, HDPE bottle | −20 ± 5° C. | 7.6 | 8.5 | 7.3 | 7.3 | 6.9 | 8.9 | 8.7 |
| 115 mg/mL, HDPE bottle | 5 ± 3° C. | 7.6 | 7.4 | 7.0 | 8.8 | NS | NS | NS |
| 150 mg/mL, Vial | | 8.0 | 6.0 | 4.7 | 7.1 | 5.4 | NS | 6.5 |
| 150 mg/mL, 2.25 mL PFS | | 7.8 | 6.7 | 6.6 | 6.2 | 7.9 | 5.3 | 5.5 |
| 150 mg/mL, 1 mL PFS | | 6.6 | 5.5 | 7.0 | 6.3 | 7.8 | 5.2 | 6.4 |
| 150 mg/mL, Vial | 25° C./60% RH | 8.0 | 6.8 | 5.9 | 7.7 | 7.7 | NS | 9.3 |
| 150 mg/mL, 2.25 mL PFS | | 7.8 | 6.6 | 7.2 | 7.7 | 9.9 | NS | NS |
| 150 mg/mL, 1 mL PFS | | 6.6 | 7.0 | 8.3 | 8.1 | 9.6 | NS | NS |
| 100 mg/mL, Vial | 40° C./75% RH | 13.3 | 11.9 | 10.0 | NS | NS | NS | NS |
| 150 mg/mL, Vial | | 8.0 | 8.9 | 6.2 | 3.3 | 0.0 | NS | NS |
| 150 mg/mL, 2.25 mL PFS | | 7.8 | 9.4 | 7.7 | 5.2 | NS | NS | NS |
| 150 mg/mL, 1 mL PFS | | 6.6 | 9.1 | 8.5 | 4.3 | NS | NS | NS |

NS = Not Scheduled

TABLE 7

| iCE results for Main (%) | | | | | | | | |
|---|---|---|---|---|---|---|---|---|
| | | Main (%) | | | | | | |
| Configuration | Storage Temperature | 0 months | 1 month | 3 months | 6 months | 12 months | 18 months | 24 months |
| 115 mg/mL, HDPE bottle | −20 ± 5° C. | 72.6 | 67.8 | 73.4 | 72.7 | 73.3 | 71.4 | 72.4 |
| 115 mg/mL, HDPE bottle | 5 ± 3° C. | 72.6 | 69.6 | 72.8 | 69.8 | NS | NS | NS |
| 150 mg/mL, Vial | | 69.3 | 72.8 | 70.6 | 69.7 | 73.4 | NS | 71.2 |
| 150 mg/mL, 2.25 mL PFS | | 69.9 | 70.2 | 70.5 | 71.3 | 67.7 | 72.0 | 71.5 |
| 150 mg/mL, 1 mL PFS | | 72.1 | 72.1 | 68.5 | 71.4 | 68.0 | 72.4 | 70.6 |
| 150 mg/mL, Vial | 25° C./60% RH | 69.3 | 70.0 | 64.4 | 58.0 | 49.4 | NS | 31.5 |
| 150 mg/mL, 2.25 mL PFS | | 69.9 | 68.1 | 64.3 | 57.8 | 46.3 | NS | NS |
| 150 mg/mL, 1 mL PFS | | 72.1 | 68.3 | 62.8 | 58.0 | 45.4 | NS | NS |
| 100 mg/mL, Vial | 40° C./75% RH | 68.3 | 53.1 | 31.8 | NS | NS | NS | NS |
| 150 mg/mL, Vial | | 69.3 | 53.1 | 29.2 | 14.4 | 4.0 | NS | NS |
| 150 mg/mL, 2.25 mL PFS | | 69.9 | 50.2 | 30.3 | 14.0 | NS | NS | NS |
| 150 mg/mL, 1 mL PFS | | 72.1 | 51.0 | 29.1 | 11.6 | NS | NS | NS |

NS = Not Scheduled

TABLE 8

| Inhibition Assay results for Relative Potency (%) | | | | | | | | |
|---|---|---|---|---|---|---|---|---|
| | | Relative Potency (%) | | | | | | |
| Configuration | Storage Temperature | 0 months | 1 month | 3 months | 6 months | 12 months | 18 months | 24 months |
| 115 mg/mL, HDPE bottle | −20 ± 5° C. | 118 | 109 | 109 | 106 | 101 | 107 | 109 |
| 115 mg/mL, HDPE bottle | 5 ± 3° C. | 118 | 111 | 111 | 105 | NS | NS | NS |
| 150 mg/mL, Vial | | 98 | 99 | 97 | 106 | 99 | NS | 107 |
| 150 mg/mL, 2.25 mL PFS | | 108 | 111 | 102 | 99 | 94 | 106 | 106 |

TABLE 8-continued

| Inhibition Assay results for Relative Potency (%) | | | | | | | | |
|---|---|---|---|---|---|---|---|---|
| | | Relative Potency (%) | | | | | | |
| Configuration | Storage Temperature | 0 months | 1 month | 3 months | 6 months | 12 months | 18 months | 24 months |
| 150 mg/mL, 1 mL PFS | | 106 | 120 | 115 | 99 | 108 | 103 | 104 |
| 150 mg/mL, Vial | 25° C./60% RH | 98 | 96 | 95 | 96 | 91 | NS | 97 |
| 150 mg/mL, 2.25 mL PFS | | 108 | 110 | 110 | 100 | 87 | NS | NS |
| 150 mg/mL, 1 mL PFS | | 106 | 122 | 109 | 98 | 99 | NS | NS |
| 100 mg/mL, Vial | 40° C./75% RH | NS | NS | NS | NS | NS | NS | NS |
| 150 mg/mL, Vial | | 98 | NS | NS | NS | 83 | NS | NS |
| 150 mg/mL, 2.25 mL PFS | | 108 | 106 | 95 | NS | NS | NS | NS |
| 150 mg/mL, 1 mL PFS | | 106 | 106 | 96 | NS | NS | NS | NS |

NS = Not Scheduled

The data from this study demonstrates that the anti-TFPI antibody at high concentration (100 mg/mL to 150 mg/mL) is stable in the 20 mM histidine, 85 mg/mL sucrose, 0.05 mg/mL edetate disodium dihydrate, 0.2 mg/mL polysorbate 80 at pH 5.8 formulation. Results also indicate that different container/closure systems (HDPE bottle, vial, PFS) do not impact stability of the anti-TFPI antibody.

The intended storage condition of 5±3° C., accelerated storage condition of 25° C./60% RH, and thermal stress storage condition of 40° C./75% RH were evaluated in the study. At the long-term storage condition of 5±3° C., the anti-TFPI antibody is shown to be stable for up to 24 months with no significant differences observed for any of the product quality attributes.

A slight increase in % HMMS is observed after 3 months at 25° C./60% RH and 1 month at 40° C./75% RH. Degradation was observed at 40° C./75% RH at 3 months however the magnitude is less than that seen with other IgG1 antibodies such as anti-VEGF Antibody. Table 9 compares % HMMS at 40° C./75% RH data for anti-TFPI Antibody and anti-VEGF Antibody. Qualified product-specific SE-HPLC methods were used to quantitate % HMMS for each antibody.

TABLE 9

| Comparison of anti-TFPI Antibody and anti-VEGF Antibody SE-HPLC results for high molecular mass species (% HMMS) at 40° C. | | | |
|---|---|---|---|
| Configuration | 0 months (0 weeks) | 1 month (4 weeks) | 3 months (12 weeks) |
| Anti-VEGF Antibody in Histidine 5.8 DP* | 2.1 | 3.1 | 5.6 |

TABLE 9-continued

| Comparison of anti-TFPI Antibody and anti-VEGF Antibody SE-HPLC results for high molecular mass species (% HMMS) at 40° C. | | | |
|---|---|---|---|
| Configuration | 0 months (0 weeks) | 1 month (4 weeks) | 3 months (12 weeks) |
| Anti-TFPI Antibody 100 mg/mL, Vial | 0.5 | 1.1 | 1.5 |
| Anti-TFPI Antibody 150 mg/mL, Vial | 0.6 | 1.2 | 2.1 |
| Anti-TFPI Antibody 150 mg/mL, 2.25 mL PFS | 0.5 | 0.9 | 2.1 |
| Anti-TFPI Antibody 150 mg/mL, 1 mL PFS | 0.5 | 1.0 | 2.4 |

*Data for anti-VEGF antibody obtained from Table 11 of US 2018/0000933

Although degradation is observed, anti-TFPI antibody maintains activity up to 24 months at 25° C./60% RH and 12 months at 40° C./75% RH in the 20 mM histidine, 85 mg/mL sucrose, 0.05 mg/mL edetate disodium dihydrate, 0.2 mg/mL polysorbate 80 at pH 5.8 formulation.

Example 2. Formulation Robustness Stability Study of Anti-TFPI Antibody

This example illustrates the stability of 150 mg/mL anti-TFPI antibody in the target formulation (control formulation) and anti-TFPI antibody formulated with either high or low excipient levels and pH. The formulations evaluated are shown in Table 10. The concentration of each component was confirmed with analytical testing. In this example, the anti-TFPI antibody used (TFPI-106) has a heavy chain variable region having the amino acid sequence of SEQ ID NO:18, and a light chain variable region having the amino acid sequence of SEQ ID NO:11.

TABLE 10

| Excipient and pH ranges evaluated in Formulation Robustness Study | | | | | | | |
|---|---|---|---|---|---|---|---|
| | Testing | Target DP Formulations[1] | | | | | |
| Components | Range | A | B | C | D | E | F |
| Formulation Name (Excipient/pH) | N/A | Target | Low/High | High/Low | Low/Low | High/High | Target, No PS80 |
| Histidine (mM) | +100%/−50% | 20 | 10 | 40 | 10 | 40 | 20 |
| Sucrose (mg/mL) | ±25% | 85 | 64 | 106 | 64 | 106 | 85 |

TABLE 10-continued

Excipient and pH ranges evaluated in Formulation Robustness Study

| Components | Testing Range | Target DP Formulations[1] A | B | C | D | E | F |
|---|---|---|---|---|---|---|---|
| Disodium EDTA (mg/mL) | ±25% | 0.05 | 0.038 | 0.063 | 0.038 | 0.063 | 0.05 |
| PS80 (mg/mL) | ±50% | 0.2 | 0.1 | 0.3 | 0.1 | 0.3 | N/A |
| pH | ±0.6 | 5.8 | 6.4 | 5.2 | 5.2 | 6.4 | 5.8 |

[1]Each formulation contains 150 mg/ml anti-TFPI antibody

Formulations were stored at the intended storage condition of 5±3° C., accelerated storage condition of 25° C./60% RH, and thermal stress storage condition of 40° C./75% RH for 6 months. Samples were then analyzed for quality attributes that are routinely used to monitor protein degradation using methods described herein. For example, the analysis consisted of size exclusion high performance liquid chromatography (SE-HPLC) to assess high molecular mass species (HMMS), reducing and non-reducing Capillary Gel Electrophoresis (CGE) to assess purity and fragmentation, and imaged capillary isoelectric focusing (iCE) to assess charge heterogeneity such as acidic, basic, and main species. Analysis also included evaluating the relative potency of anti-TFPI antibody using an inhibition assay. Specific analytical procedures, including compendial and non-compendial methods, were used to assess the characteristics, purity, and relative potency of the anti-TFPI antibody. Results are summarized in Tables 11-19.

TABLE 11 pH Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | pH | 5.8 | 5.8 | 5.8 | 5.8 |
| B | pH | 6.5 | 6.6 | 6.6 | 6.6 |
| C | pH | 5.2 | 5.3 | 5.3 | 5.3 |
| D | pH | 5.4 | 5.5 | 5.5 | 5.5 |
| E | pH | 6.5 | 6.5 | 6.5 | 6.5 |
| F | pH | 5.9 | 5.8 | 5.8 | 5.8 |

TABLE 12

Protein Concentration by UV Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | mg/mL | 153.7 | 154.8 | 155.9 | 157.2 |
| B | mg/mL | 152.6 | 161.9 | 158.5 | 160.4 |
| C | mg/mL | 152.4 | 160.4 | 159.3 | 159.3 |
| D | mg/mL | 153.4 | 155.7 | 153.8 | 158.3 |
| E | mg/mL | 150.2 | 158.3 | 156.5 | 160.0 |
| F | mg/mL | 152.1 | 156.3 | 157.8 | 157.5 |

TABLE 13

SE-HPLC Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | % Monomer | 99.4 | 99.3 | 97.3 | 84.0 |
| | % HMMS | 0.5 | 0.6 | 0.9 | 6.1 |
| | % LMMS | NMT 0.2 | NMT 0.2 | 1.8 | 9.9 |
| B | % Monomer | 99.2 | 99.0 | 96.3 | 79.0 |
| | % HMMS | 0.7 | 0.9 | 1.5 | 7.5 |
| | % LMMS | NMT 0.2 | NMT 0.2 | 2.2 | 13.5 |
| C | % Monomer | 99.4 | 99.4 | 96.9 | 80.5 |
| | % HMMS | 0.5 | 0.5 | 0.9 | 8.0 |
| | % LMMS | NMT 0.2 | NMT 0.2 | 2.2 | 11.6 |
| D | % Monomer | 99.3 | 99.3 | 97.2 | 84.6 |
| | % HMMS | 0.6 | 0.7 | 1.0 | 5.5 |
| | % LMMS | NMT 0.2 | NMT 0.2 | 1.9 | 9.9 |
| E | % Monomer | 99.3 | 99.3 | 96.7 | 83.5 |
| | % HMMS | 0.6 | 0.7 | 1.1 | 5.5 |
| | % LMMS | NMT 0.2 | NMT 0.2 | 2.1 | 11.0 |
| F | % Monomer | 99.3 | 99.4 | 97.4 | 85.0 |
| | % HMMS | 0.5 | 0.6 | 0.9 | 5.3 |
| | % LMMS | NMT 0.2 | NMT 0.2 | 1.7 | 9.6 |

TABLE 14

Non-Reducing CGE Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | % IgG | 98.4 | 98.2 | 95.7 | 71.3 |
| | % Fragments | 1.6 | 1.8 | 4.3 | 26.6 |
| B | % IgG | 98.6 | 97.9 | 95.4 | 67.4 |
| | % Fragments | 1.4 | 2.1 | 4.2 | 30.8 |
| C | % IgG | 98.0 | 97.8 | 95.9 | 66.2 |
| | % Fragments | 2.0 | 2.2 | 4.1 | 30.9 |
| D | % IgG | 98.0 | 97.8 | 96.4 | 72.1 |
| | % Fragments | 2.0 | 2.2 | 3.6 | 26.5 |
| E | % IgG | 97.8 | 97.6 | 95.4 | 74.0 |
| | % Fragments | 2.2 | 2.4 | 4.6 | 24.6 |
| F | % IgG | 97.8 | 97.5 | 96.3 | 72.2 |
| | % Fragments | 2.2 | 2.5 | 3.7 | 25.6 |

TABLE 15

Reducing CGE Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | % Heavy + Light Chain | 98.2 | 97.0 | 95.6 | 85.7 |
| | % Fragments | NMT 0.3 | 0.7 | 2.1 | 10.7 |
| B | % Heavy + Light Chain | 98.2 | 97.4 | 94.4 | 81.5 |
| | % Fragments | NMT 0.3 | 0.4 | 2.4 | 10.8 |
| C | % Heavy + Light Chain | 98.2 | 97.4 | 95.2 | 85.2 |
| | % Fragments | 0.8 | NMT 0.3 | 2.5 | 12.3 |
| D | % Heavy + Light Chain | 98.2 | 97.4 | 95.4 | 85.9 |
| | % Fragments | NMT 0.3 | 0.4 | 2.3 | 11.2 |
| E | % Heavy + Light Chain | 97.4 | 96.9 | 95.0 | 83.4 |
| | % Fragments | 0.8 | 0.8 | 2.0 | 10.1 |
| F | % Heavy + Light Chain | 98.2 | 97.2 | 95.6 | 86.5 |
| | % Fragments | NMT 0.3 | 0.7 | 2.2 | 10.3 |

TABLE 16 iCE Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | % Main | 73.8 | 70.7 | 57.5 | 12.9 |
| | % Acidic | 19.6 | 23.5 | 34.1 | 82.7 |
| | % Basic | 6.6 | 5.7 | 8.4 | 4.3 |

TABLE 16-continued iCE Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| B | % Main | 73.7 | 69.8 | 54.5 | 12.7 |
| | % Acidic | 20.9 | 24.3 | 38.7 | 82.6 |
| | % Basic | 5.4 | 5.9 | 6.8 | 4.8 |
| C | % Main | 72.8 | 70.0 | 53.6 | 11.6 |
| | % Acidic | 20.7 | 23.9 | 35.4 | 83.3 |
| | % Basic | 6.5 | 6.1 | 10.9 | 5.1 |
| D | % Main | 72.4 | 70.9 | 56.8 | 14.6 |
| | % Acidic | 20.2 | 22.9 | 33.7 | 80.3 |
| | % Basic | 7.4 | 6.2 | 9.5 | 5.1 |
| E | % Main | 71.8 | 69.2 | 53.6 | 9.6 |
| | % Acidic | 22.3 | 25.1 | 39.6 | 86.9 |
| | % Basic | 5.8 | 5.8 | 6.8 | 3.5 |
| F | % Main | 73.1 | 72.5 | 57.4 | 13.2 |
| | % Acidic | 20.2 | 21.6 | 35.0 | 81.9 |
| | % Basic | 6.7 | 5.9 | 7.6 | 4.9 |

TABLE 17

Methionine Oxidation Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | % Oxidation | 2.0 | 1.5 | 2.7 | 12.3 |
| B | % Oxidation | 1.0 | 1.3 | 2.6 | 7.4 |
| C | % Oxidation | 1.1 | 1.4 | 2.7 | 19.5 |
| D | % Oxidation | 1.2 | 1.3 | 2.1 | 10.7 |
| E | % Oxidation | 1.2 | 1.5 | 3.4 | 8.8 |
| F | % Oxidation | 1.3 | 1.3 | 3.0 | 12.3 |

TABLE 18

Appearance Results** with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | Color | ≤B7 | ≤B6 | ≤B6 | ≤BY2 |
| | Clarity† | ≤Ref. II | ≤Ref. III | ≤Ref. III | ≤Ref. III |
| | Visible particulates | EFVP* | EFVP | EFVP | EFVP |
| | Color | ≤B7 | ≤B6 | ≤B6 | ≤BY4 |
| B | Clarity† | ≤Ref. III | ≤Ref. II | ≤Ref. III | ≤Ref. III |
| | Visible particulates | EFVP | EFVP | 2 small white particles | 1 medium white particle |
| | Color | ≤B7 | ≤B6 | ≤B6 | ≤BY1 |
| C | Clarity† | ≤Ref. II | ≤Ref. III | ≤Ref. III | ≤Ref. III |
| | Visible particulates | EFVP | EFVP | EFVP | EFVP |
| D | Color | ≤B7 | ≤B6 | ≤B6 | ≤BY4 |
| | Clarity† | ≤Ref. II | ≤Ref. III | ≤Ref. III | ≤Ref. III |
| | Visible particulates | EFVP | 1 small white particle | 1 small white particle | 2 small white particles |
| E | Color | ≤B7 | Not tested | ≤B6 | ≤BY1 |
| | Clarity† | ≤Ref. II | ≤Ref. III | ≤Ref. III | ≤Ref. III |
| | Visible particulates | EFVP | EFVP | 1 small white particle | 1 small particle |

TABLE 18-continued

Appearance Results** with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| F | Color | ≤B7 | ≤B6 | ≤B6 | ≤BY3 |
| | Clarity† | ≤Ref. II | ≤Ref. IV | ≤Ref. IV | ≤Ref. III |
| | Visible particulates | EFVP | Numerous small white particles | Numerous small white particles | Numerous particles but not as many as 5 and 25° C. |

*EFVP: Essentially free from visible particulates

**Clarity and coloration assessed in accordance with the current European Pharmacopoeia procedure, Ph. Eur. 2.2.1 and Ph. Eur. 2.2.2, respectively.

†Ref. II, Ref. III, and Ref. IV are equivalent to 6 NTU, 18 NTU, and 30 NTU respectively

TABLE 19

Inhibition Assay Results with up to 6 Months of Data at 5° C., 25° C., and 40° C.

| Formulation | Attribute | 0 months | 5° C. 6 months | 25° C. 6 months | 40° C. 6 months |
|---|---|---|---|---|---|
| A | % Relative Potency | 108 | 104 | 97 | 86 |
| B | % Relative Potency | 102 | 110 | 106 | 97 |
| C | % Relative Potency | 101 | 110 | 109 | 86 |
| D | % Relative Potency | 101 | 108 | 90 | 88 |
| E | % Relative Potency | 102 | 101 | 111 | 93 |
| F | % Relative Potency | 99 | 99 | 114 | 93 |

The data shown in Tables 11-19 and described below demonstrates that anti-TFPI antibody formulations containing either high excipients or low excipient or pH levels are stable after 6 months under both real-time stability conditions.

Appearance

After 6 months of storage at 2-8° C. and 25° C. (Table 18), no significant changes in color, clarity, and visible particles were observed for most of the formulations (A-E). After 6 months of storage at 2-8° C. and 25° C., a significant increase in visible particulates was observed for the PS80-free formulation F.

After 6 months of storage at of 40° C., significant changes in solution color were observed across all formulations (A-F). This result is expected upon storage at the accelerated stress condition based on previous stability studies. These effects were most pronounced for formulations C and E which contained higher excipient concentrations relative to the target formulation. No major changes in solution clarity were observed. For formulation A-E, occasional visible particles were observed however these may be attributed to sample handling. After 6 months at 40° C. a significant increase in visible particles was observed for the PS80-free formulation F, although it was noted that the increase was less drastic than the 2-8° C. and 25° C. storage conditions. This finding highlights the importance of including PS80 in the drug product formulation.

pH

After 6 months of storage at 2-8° C., 25° C., and 40° C. (Table 11), no significant changes in pH were observed across all formulations (A-F).

Protein Concentration by UV

After 6 months of storage at 2-8° C., 25° C., and 40° C. (Table 12), protein concentration remained within the 150 mg/mL±15 mg/mL specification. For most formulation and storage conditions, a minor increase in protein concentration was observed which may be attributed to assay variability.

Size Exclusion Chromatography (SE-HPLC)

After 6 months of storage at 2-8° C. (Table 13), no significant changes in % HMMS and % Monomer, were observed for all formulations (A-F). It was noted that peaks corresponding to low molecular weight species were inconsistently observed during storage at 2-8° C. across all formulations.

After 6 months of storage at 25° C., a minor increase of 1-2% in both % HMMS and % LMMS and corresponding decrease in % Monomer was observed for all formulations (A-F). All % HMMS results remained below the acceptance criteria of 5%.

After 6 months of storage at 40° C., a significant increase in % HMMS and % LMMS and corresponding decrease in % Monomer was observed for all formulations (A-F). Formulations B (low excipient/high pH) and C (high excipient/low pH) exhibited the greatest decrease in % Monomer, about 20%. These results are expected at the accelerated stress condition based on previous stability studies.

Non-Reducing Capillary Gel Electrophoresis (nrCGE)

After 6 months of storage at 2-8° C. (Table 14), no significant changes in % IgG, % Fragment, and % Other were observed for all formulations (A-F).

After 6 months of storage at 25° C., a minor increase of 2-3% Fragment and corresponding decrease in % IgG was observed for all formulations (A-F). No significant changes in % Other were observed.

After 6 months of storage at 40° C. a significant increase of >25% Fragment and corresponding decrease in % IgG was observed for all formulation (A-F). The greatest increases in % Fragment, >30% were observed for Formulations B (low excipient/high pH) and C (high excipient/low pH). This result is consistent with the SE-HPLC results. Minor increases in % Other were observed across all formulations.

Reducing Capillary Gel Electrophoresis (rCGE)

After 6 months of storage at 2-8° C. (Table 15), no significant changes in % Heavy chain+light chain (HC+LC), % Fragment, and % Other were observed for all formulations (A-F).

After 6 months of storage at 25° C., a minor increase of 1-2% Fragment and corresponding decrease in % HC+LC was observed for all formulations (A-F). A minor increase of 1% Other was observed for only for formulation B and E.

After 6 months of storage at 40° C. a significant increase of approximately 10% Fragment and corresponding decrease in % HC+LC was observed for all formulation (A-F). The greatest increase in % Fragment was observed for formulation C (high excipient/low pH). Most formulations (A, C, D, and F) showed a minor increase of 2-3% Other. By contrast a significant increase in % Other of 7-8% was observed for formulations B and E.

Isoelectric Focusing Capillary Electrophoresis (iCE)

After 6 months of storage at 2-8° C. (Table 16), a minor increase in % Acidic and corresponding decrease in % Main was observed across all formulations (A-F) whereas no significant changes in % Basic were observed.

After 6 months of storage at 25° C., a significant increase of 10-20% Acidic and corresponding decrease in % Main was observed across all formulations. A minor increase of 2-3% Basic was observed across most formulations. The high pH formulations B and E exhibited the greatest increase in % Acidic, ~18%. This finding may be explained by the pH-dependence of asparagine deamidation, described in-detail elsewhere[9]

After 6 months of storage at 40° C., a significant increase of ~60% Acidic and corresponding decrease in % Main was observed across all formulations. The greatest increase in % Acidic was observed for formulation E which may be explained by the pH-dependence of asparagine deamidation. A net decrease in % Basic was observed across all formulations comparing the T=0 and T=6 months samples.

Methionine Oxidation

After 6 months of storage at 2-8° C. (Table 17), no significant change in % MetOx was observed across all formulations (A-F). After 6 months of storage at 25° C., a minor increase of 1-2% MetOx was observed across all formulations (A-F). After 6 months of storage at 40° C., a significant increase of about 10% MetOX was observed across all formulations. The greatest increase in % MetOX was observed for formulation C (high excipient/low pH), ~20%.

Inhibition Bioassay

After 6 months of storage at 2-8° C. and 25° C. (Table 19), no significant changes in % Relative Potency were observed across all formulation. After 6 months of storage at 40° C. a decreasing trend in Relative Potency was observed for formulations A, C, D, and E, however, all results remained within the acceptance criteria.

Thus, although degradation is observed, anti-TFPI antibody maintains activity at accelerated storage condition of 25° C./60% RH, and thermal stress storage condition of 40° C./75% RH for 6 months in all formulations (Table 19).

Agitation Study

An agitation study was conducted by filling 1 mL of formulations A-F into 1 mL long syringes with staked needles. The syringes were then subjected to 48 hours of agitation stress. The agitation study was conducted at ambient room temperature (~22° C.) with the syringes placed in a horizontal orientation and agitated using an orbital shaker set to 300 rpm. The Time Zero (TO) control was not exposed to shaking stress.

After 48 hours of agitation 300 rpm, no significant changes were observed across all formulation (A-F) by SE-HPLC, nrCGE, rCGE, iCE, and Methionine Oxidation. A significant increase in visible particles was observed for the PS80-free formulation F, confirming the importance of PS80 in the DP formulation. No changes in appearance were observed for most formulations (A-E).

CONCLUSION

The goal of this study was to establish a design space and to demonstrate that product quality is robust to variations in formulation composition and agitation. After 6 months of storage, variations in formulation had minimal impact on the DP stability at the intended storage temperature of 2-8° C. for most formulations (A-E). A significant increase in visible and sub-visible particles was observed for the PS80-free formulation (F), confirming the importance of PS80 in the DP formulation. At 25° C. and 40° C., changes in product quality were observed beginning at 3 months for 25° C. and 1 month for 40° C. which are expected under accelerated stress conditions based on previous stability studies. Results from 40° C. storage suggest that protein aggregation reaches a maximum at the corners of the design space (B and C) and that deamidation reaches a maximum at high pH (B and E). All formulations showed robustness to agitation stress except for the PS80-free formulation F. These results demonstrate the robustness of the DP to variation of excipient levels outside of what is expected in the process. The formulations evaluated are comparable to the formulation containing the target excipient levels (Control formulation A) therefore demonstrating formulation robustness.

TABLE 20

Sequences

| Seq ID | Description | Sequence |
|---|---|---|
| 1 | Human TFPIα K1K2 (Accession #P10646, residues 29-177) | DSEEDEEHTI ITDTELPPLK LMHSFCAFKA DDGPCKAIMK RFFFNIFTRQ CEEFIYGGCE GNQNRFESLE ECKKMCTRDN ANRIIKTTLQ QEKPDFCFLE EDPGICRGYI TRYFYNNQTK QCERFKYGGC LGNMNNFETL EECKNICED |
| 2 | Human TFPIα K1K2K3 (Accession #P10646, residues 29-282) | DSEEDEEHTI ITDTELPPLK LMHSFCAFKA DDGPCKAIMK RFFFNIFTRQ CEEFIYGGCE GNQNRFESLE ECKKMCTRDN ANRIIKTTLQ QEKPDFCFLE EDPGICRGYI TRYFYNNQTK QCERFKYGGC LGNMNNFETL EECKNICEDG PNGFQVDNYG TQLNAVNNSL TPQSTKVPSL FEFHGPSWCL TPADRGLCRA NENRFYYNSV IGKCRPFKYS GCGGNENNFT SKQECLRACK KGFIQRISKG GLIK |

TABLE 20-continued

| Seq ID | Description | Sequence |
|---|---|---|
| 3 | Human TFPI2 K1K2K3 (Accession #P48307.1, residues 23-211) | DAAQEPTGNN AEICLLPLDY GPCRALLLRY YYDRYTQSCR QFLYGGCEGN ANNFYTWEAC DDACWRIEKV PKVCRLQVSV DDQCEGSTEK YFFNLSSMTC EKFFSGGCHR NRIENRFPDE ATCMGFCAPK KIPSFCYSPK DEGLCSANVT RYYFNPRYRT CDAFTYTGCG GNDNNFVSRE DCKRACAKA |
| 4 | Mouse TFPI K1K2 (Accession #O54819, residues 29-174) | LSEEADDTDS ELGSMKPLHT FCAMKADDGP CKAMIRSYFF NMYTHQCEEF IYGGCEGNEN RFDTLEECKK TCIPGYEKTA VKAASGAERP DFCFLEEDPG LCRGYMKRYL YNNQTKQCER FVYGGCLGNR NNFETLDECK KICENP |
| 5 | Cynomolgus Monkey TFPI K1K2 (Accession #Q2PFV4, residues 29-177) | DSEEDEEYTI ITDTELPPLK LMHSFCAFKP DDGPCKAIMK RFFFNIFTRQ CEEFIYGGCG GNQNRFESME ECKKVCTRDN VNRIIQTALQ KEKPDFCFLE EDPGICRGYI TRYFYNNQSK QCERFKYGGC LGNMNNFETL EECKNTCED |
| 6 | Rabbit TFPI K1K2 (Accession #P19761, residues 29-173) | AAEEDEEFTN ITDIKPPLQK PTHSFCAMKV DDGPCRAYIK RFFFNILTHQ CEEFIYGGCE GNENRFESLE ECKEKCARDY PKMTTKLTFQ KGKPDFCFLE EDPGICRGYI TRYFYNNQSK QCERFKYGGC LGNLNNFESL EECKNTCEN |
| 7 | Rat TFPI K1K2 (Accession #Q02445, residues 29-176) | LPEEDDDTIN TDSELRPMKP LHTFCAMKAE DGPCKAMIRS YYFNMNSHQC EEFIYGGCRG NKNRFDTLEE CRKTCIPGYK KTTIKTTSGA EKPDFCFLEE DPGICRGFMT RYFYNNQSKQ CEQFKYGGCL GNSNNFETLE ECRNTCED |
| 8 | mAb-TFPI-23 LC CDR1 mAb-TFPI-106 LC CDR1 mAb-TFPI-107 LC CDR1 | TGSSSNIGAG YDVH |
| 9 | mAb-TFPI-23 LC CDR2 mAb-TFPI-106 LC CDR2 mAb-TFPI-107 LC CDR2 | GNSNRPS |
| 10 | mAb-TFPI-23 LC CDR3 mAb-TFPI-106 LC CDR3 mAb-TFPI-107 LC CDR3 | QSYDSSLSGS GV |
| 11 | mAb-TFPI-23 VL mAb-TFPI-106 VL mAb-TFPI-107 VL CDR1, CDR2, CDR3 are underlined | QSVLTQPPSV SGAPGQRVTI SCTGSSSNIG AGYDVHWYQQ LPGTAPKLLI YGNSNRPSGV PDRFSGSKSG TSASLAITGL QAEDEADYYC QSYDSSLSGS GVFGGGTKLT VLG |
| 12 | mAb-TFPI-23 LC mAb-TFPI-106 LC mAb-TFPI-107 LC CDR1,2, 3 are underlined. Variable sequence in italics | QSVLTQPPSV SGAPGQRVTI SCTGSSSNIG AGYDVHWYQQ LPGTAPKLLI YGNSNRPSGV PDRFSGSKSG TSASLAITGL QAEDEADYYC QSYDSSLSGS GVFGGGTKLT VLGQPKAAPS VTLFPPSSEE LQANKATLVC LISDFYPGAV TVAWKADSSP VKAGVETTTP SKQSNNKYAA SSYLSLTPEQ WKSHRSYSCQ VTHEGSTVEK TVAPTECS |
| 13 | mAb-TFPI-23 HC CDR1 mAb-TFPI-106 HC CDR1 mAb-TFPI-107 HC CDR1 | GFTFSSYAMS |

TABLE 20-continued

| Seq ID | Description | Sequence |
|---|---|---|
| 14 | mAb-TFPI-23 HC CDR2<br>mAb-TFPI-106 HC CDR2<br>mAb-TFPI-107 HC CDR2 | AISGSGGSTY YADSVKG |
| 15 | mAb-TFPI-23 HC CDR3<br>mAb-TFPI-106 HC CDR3<br>mAb-TFPI-107 HC CDR3 | LGATSLSAFD I |
| 16 | mAb-TFPI-23 VH CDR1, CDR2, CDR3 are underlined | QVQLVESGGG LVQPGGSLRL SCAASGFTFS<br>SYAMSWWRQA PGKGLEWWSA ISGSGGSTYY<br>ADSVKGRFTI SRDNSKNTLY LQMNSLRAED<br>TAVYYCAILG ATSLSAFDIW GQGTMVTVSS |
| 17 | mAb-TFPI-23 HC CDR1, CDR2 and CDR3 underlined. Variable sequence in italics. Effector function mutations in bold. | *QVQLVESGGG LVQPGGSLRL SCAASGFTFS*<br>*SYAMSWVRQA PGKGLEWVSA ISGSGGSTYY*<br>*ADSVKGRFTI SRDNSKNTLY LQMNSLRAED*<br>*TAVYYCAILG ATSLSAFDIW GQGTMVTVSS*<br>ASTKGPSVFP LAPSSKSTSG GTAALGCLVK<br>DYFPEPVTVS WNSGALTSGV HTFPAVLQSS<br>GLYSLSSVVT VPSSSLGTQT YICNVNHKPS<br>NTKVDKKVEP KSCDKTHTCP PCPAPE**AAGA**<br>PSVFLFPPKP KDTLMISRTP EVTCVVVDVS<br>HEDPEVKFNW YVDGVEVHNA KTKPREEQYN<br>STYRVVSVLT VLHQDWLNGK EYKCKVSNKA<br>LPAPIEKTIS KAKGQPREPQ VYTLPPSREE<br>MTKNQVSLTC LVKGFYPSDI AVEWESNGQP<br>ENNYKTTPPV LDSDGSFFLY SKLTVDKSRW<br>QQGNVFSCSV MHEALHNHYT QKSLSLSPG |
| 18 | mAb-TFPI-106 VH Human Ig lamda CL with Q1E, V5L mutations in bold | **E**VQL**L**ESGGG LVQPGGSLRL SCAASGFTFS<br>SYAMSWVRQA PGKGLEWVSA ISGSGGSTYY<br>ADSVKGRFTI SRDNSKNTLY LQMNSLRAED<br>TAVYYCAILG ATSLSAFDIW GQGTMVTVSS |
| 19 | mAb-TFPI-106 HC CDR1, CDR2 and CDR3 underlined. Variable sequence in italics. Q1E, V5L mutations in bold. Effector function mutations in bold. | ***E****VQL****L****ESGGG LVQPGGSLRL SCAASGFTFS*<br>*SYAMSWVRQA PGKGLEWVSA ISGSGGSTYY*<br>*ADSVKGRFTI SRDNSKNTLY LQMNSLRAED*<br>*TAVYYCAILG ATSLSAFDIW GQGTMVTVSS*<br>ASTKGPSVFP LAPSSKSTSG GTAALGCLVK<br>DYFPEPVTVS WNSGALTSGV HTFPAVLQSS<br>GLYSLSSVVT VPSSSLGTQT YICNVNHKPS<br>NTKVDKKVEP KSCDKTHTCP PCPAPE**AAGA**<br>PSVFLFPPKP KDTLMISRTP EVTCVVVDVS<br>HEDPEVKFNW YVDGVEVHNA KTKPREEQYN<br>STYRVVSVLT VLHQDWLNGK EYKCKVSNKA<br>LPAPIEKTIS KAKGQPREPQ VYTLPPSREE<br>MTKNQVSLTC LVKGFYPSDI AVEWESNGQP<br>ENNYKTTPPV LDSDGSFFLY SKLTVDKSRW<br>QQGNVFSCSV MHEALHNHYT QKSLSLSPG |
| 20 | mAb-TFPI-107 VH Human Ig lamda CL with Q1E, V5L, I94K mutations in bold | **E**VQL**L**ESGGG LVQPGGSLRL SCAASGFTFS<br>SYAMSWVRQA PGKGLEWVSA ISGSGGSTYY<br>ADSVKGRFTI SRDNSKNTLY LQMNSLRAED<br>TAVYYCA**K**LG ATSLSAFDIW GQGTMVTVSS |
| 21 | mAb-TFPI-107 HC CDR1, CDR2 and CDR3 underlined. Variable sequence in italics. Q1E, V5L, I94K mutations in bold. Effector function mutations in bold. | ***E****VQL****L****ESGGG LVQPGGSLRL SCAASGFTFS*<br>*SYAMSWVRQA PGKGLEWVSA ISGSGGSTYY*<br>*ADSVKGRFTI SRDNSKNTLY LQMNSLRAED*<br>*TAVYYCA****K****LG ATSLSAFDIW GQGTMVTVSS*<br>ASTKGPSVFP LAPSSKSTSG GTAALGCLVK<br>DYFPEPVTVS WNSGALTSGV HTFPAVLQSS<br>GLYSLSSVVT VPSSSLGTQT YICNVNHKPS<br>NTKVDKKVEP KSCDKTHTCP PCPAPE**AAGA**<br>PSVFLFPPKP KDTLMISRTP EVTCVWVDVS<br>HEDPEVKFNW YVDGVEVHNA KTKPREEQYN<br>STYRVVSVLT VLHQDWLNGK EYKCKVSNKA<br>LPAPIEKTIS KAKGQPREPQ VYTLPPSREE |

TABLE 20-continued

| Seq ID | Description | Sequence |
|---|---|---|
| Sequences | | |
| | | MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 22 | 2A8-200 LC CDR1, CDR2, CDR3 underlined Variable sequence in italics | *DIELTQPPSV SVAPGQTARI SCSGDNLRNY YAHWYQQKPG QAPVVVIFYD VNRPSGIPER FSGSNSGNTA TLTISGTQAE DEADYYCQSW WDGVPVFGGG* TKLTVLGQPK AAPSVTLFPP SSEELQANKA TLVCLISDFY PGAVTVAWKA DSSPVKAGVE TTTPSKQSNN KYAASSYLSL TPEQWKSHRS YSCQVTHEGS TVEKTVAPTE CS |
| 23 | 2A8-200 HC CDR1, CDR2, CDR3 underlined Variable sequence in italics | *QVQLVESGGG LVQPGGSLRL SCAASGFTFR SYGMDWVRQA PGKGLEWVSS IRGSRSSTYY ADSVKGRFTI SRDNSKNTLY LQMNSLRAED TAVYYCARLY RYWFDYWGQG TLVTVSS*AST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 24 | hz4F36 LC CDR1, CDR2, CDR3 underlined Variable sequence in italics | *DIVMTQTPLS LSVTPGQPAS ISCKSSQSLL ESDGKTYLNW YLQKPGQSPQ LLIYLVSILD SGVPDRFSGS GSGTDFTLKI SRVEAEDVGV YYCLQATHFP QTFGGGTKVE IK*RTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 25 | hz4F36 HC CDR1, CDR2, CDR3 underlined Variable sequence in italics | *EVQLVESGGG LVKPGGSLRL SCAASGFTFS NYAMSWVRQT PEKRLEWVAT ISRSGSYSYF PDSVQGRFTI SRDNAKNSLY LQMNSLRAED TAVYYCARLG GYDEGDAMDS WGQGTTVTVS S*ASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |

The various features and embodiments of the present invention, referred to in individual sections above apply, as appropriate, to other sections, mutatis mutandis. Consequently features specified in one section may be combined with features specified in other sections, as appropriate. All references cited herein, including patents, patent applications, papers, text books, and cited sequence Accession numbers, and the references cited therein are hereby incorporated by reference in their entirety. In the event that one or more of the incorporated literature and similar materials differs from or contradicts this application, including but not limited to defined terms, term usage, described techniques, or the like, this application controls.

PCT (Original in Electronic Form)

| | | |
|---|---|---|
| 0-1 | **Form PCT/RO/134 Indications Relating to Deposited Microorganism(s) or Other Biological Material (PCT Rule 13bis)** | |
| 0-1-1 | Prepared Using | **ePCT-Filing Version 4.7.108 MT/FOP 20201020/1.1** |
| 0-2 | **International Application No.** | PCT/IB2020/060571 |
| 0-3 | **Applicant's or agent's file reference** | **PC072541A** |

| | | |
|---|---|---|
| 1 | **The indications made below relate to the deposited microorganism(s) or other biological material referred to in the description on:** | |
| 1-1 | **page** | **8** |
| 1-2 | **line** | **16** |
| 1-3 | **Identification of deposit** | |
| 1-3-1 | Name of depositary institution | **ATCC American Type Culture Collection** |
| 1-3-2 | Address of depositary institution | **American Type Culture Collection (ATCC) 10801 University Blvd. Manassas, Virginia 20110-2209 United States of America** |
| 1-3-3 | Date of deposit | **18 August 2015 (18.08.2015)** |
| 1-3-4 | Accession Number | **ATCC 122329** |
| 1-4 | **Additional Indications** | **Page 8 Line 22** |
| 1-5 | **Designated States for Which Indications are Made** | **All designations** |
| 1-6 | **Separate Furnishing of Indications** These indications will be submitted to the International Bureau later | |
| 2 | **The indications made below relate to the deposited microorganism(s) or other biological material referred to in the description on:** | |
| 2-1 | **page** | **8** |
| 2-2 | **line** | **19** |
| 2-3 | **Identification of deposit** | |
| 2-3-1 | Name of depositary institution | **ATCC American Type Culture Collection** |
| 2-3-2 | Address of depositary institution | **American Type Culture Collection (ATCC) 10801 University Blvd. Manassas, Virginia 20110-2209 United States of America** |
| 2-3-3 | Date of deposit | **18 August 2015 (18.08.2015)** |
| 2-3-4 | Accession Number | **ATCC 122328** |
| 2-4 | **Additional Indications** | **Page 8 Line 23** |
| 2-5 | **Designated States for Which Indications are Made** | **All designations** |
| 2-6 | **Separate Furnishing of Indications** These indications will be submitted to the International Bureau later | |

PCT (Original in Electronic Form)

FOR RECEIVING OFFICE USE ONLY

| | | |
|---|---|---|
| **0-4** | **This form was received with the international application:** (yes or no) | |
| 0-4-1 | Authorized officer | |

FOR INTERNATIONAL BUREAU USE ONLY

| | | |
|---|---|---|
| **0-5** | **This form was received by the international Bureau on:** | |
| 0-5-1 | Authorized officer | |

BUDAPEST RESTRICTED CERTIFICATE OF DEPOSIT
BUDAPEST TREATY ON THE INTERNATIONAL RECOGNITION OF THE DEPOSIT OF MICROORGANISMS FOR THE PURPOSES OF PATENT PROCEDURE
INTERNATIONAL FORM
RECEIPT IN THE CASE OF AN ORIGINAL DEPOSIT ISSUED PURSUANT TO RULE 7.3 AND VIABILITY STATEMENT ISSUED PURSUANT TO RULE 10.2

The American Type Culture Collection (ATCC®) has received your deposit of seeds/strain(s)/strain(s) in connection with the filing of an application for patent. The following information is provided to fulfill Patent Office requirements.

Debra Pittman
Pfizer, Inc.
610 Main St.
Cambridge, MA 02139

Deposited on Behalf of: Pfizer, Inc.

Date of Receipt of seeds/strain(s) by the ATCC®: July 22, 2015

Depositor Reference: pUC vector with DNA insert encoding human antibody light chain

Strain: mAb-TFPI-106 VL

Quantiry: 25 Vials

ATCC Designation: PTA-122328

The ATCC® understands that:

1. The deposit of these strain(s) does not grant ATCC® a license, either express or implied, to infringe the patent, and our release of these strain(s) to others does not grant them a license, either express or implied, to infringe the patent.

2. If the deposit should die or be destroyed during the effective term of the patent, it shall be your responsibility to replace it with viable material. It is also your responsibility to supply a sufficient quantity for distribution for the deposit term. ATCC® will distribute and maintain the material for 30 years or 5 years following the most recent request for the deposit, whichever is longer. The United States and many other countries are signatory to the Budapest Treaty.

Prior to the issuance of a U.S. Patent, the ATCC® agrees in consideration for a one-time service charge, not to distribute these strain(s) or any information relating thereto or to their deposit except as instructed by the depositor or relevant patent office. After relevant patent issues we are responsible to release the strain(s) and they will be made available for distribution to the public without any restrictions. We will inform you of requests for the strain(s) for 30 years from date of deposit.

ATCC®

The deposit was tested 08/18/2015 and on that date, the strain(s) were viable
International Depository Authority: American Type Culture Collection (ATCC®), Manassas, VA, USA Signature of person having authority to represent ATCC®:

Michiyo Gilpin

August 19, 2015
Date cc: Cynthia T. Chen

Ref: Docket or Case No: PC72096

ATCC®

BUDAPEST RESTRICTED CERTIFICATE OF DEPOSIT
BUDAPEST TREATY ON THE INTERNATIONAL RECOGNITION OF
THE DEPOSIT OF MICROORGANISMS FOR THE PURPOSES OF PATENT PROCEDURE
INTERNATIONAL FORM
RECEIPT IN THE CASE OF AN ORIGINAL DEPOSIT ISSUED PURSUANT TO RULE 7.3
AND VIABILITY STATEMENT ISSUED PURSUANT TO RULE 10.2

The American Type Culture Collection (ATCC®) has received your deposit of seeds/strain(s)/strain(s) in connection with the filing of an application for patent. The following information is provided to fulfill Patent Office requirements.

Debra Pittman
Pfizer, Inc.
610 Main St.
Cambridge, MA 02139

Deposited on Behalf of: Pfizer, Inc.

Date of Receipt of seeds/strain(s) by the ATCC®: July 22, 2015

Depositor Reference: pUC vector with DNA insert encoding human antibody heavy chain

Strain: mAb-TFPI-106 VH

Quantiry: 25 Vials

ATCC Designation: PTA-122329

The ATCC® understands that:

1. The deposit of these strain(s) does not grant ATCC® a license, either express or implied, to infringe the patent, and our release of these strain(s) to others does not grant them a license, either express or implied, to infringe the patent.

2. If the deposit should die or be destroyed during the effective term of the patent, it shall be your responsibility to replace it with viable material. It is also your responsibility to supply a sufficient quantity for distribution for the deposit term. ATCC® will distribute and maintain the material for 30 years or 5 years following the most recent request for the deposit, whichever is longer. The United States and many other countries are signatory to the Budapest Treaty.

Prior to the issuance of a U.S. Patent, the ATCC® agrees in consideration for a one-time service charge, not to distribute these strain(s) or any information relating thereto or to their deposit except as instructed by the depositor or relevant patent office. After relevant patent issues we are responsible to release the strain(s) and they will be made available for distribution to the public without any restrictions. We will inform you of requests for the strain(s) for 30 years from date of deposit.

ATCC

The deposit was tested 08/18/2015 and on that date, the strain(s) were viable
International Depository Authority: American Type Culture Collection (ATCC®), Manassas, VA, USA Signature of person having authority to represent ATCC®:

Michiyo Gilpin

August 19, 2015
Date cc: Cynthia T. Chen

Ref: Docket or Case No: PC72096

We claim:

1. A stable pharmaceutical formulation consisting of: about 100 mg/mL to about 150 mg/mL of an antibody that specifically binds to an epitope in Kunitz Domain 2 (K2) of Tissue Factor Pathway Inhibitor (TFPI), about 20 mM histidine buffer, about 85 mg/mL sucrose, about 0.2 mg/mL polysorbate 80 and about 0.05 mg/mL disodium edetate dihydrate (EDTA), wherein the formulation has a pH at about 5.8, wherein the histidine buffer comprises L-histidine, L-histidine monohydrochloride or a mixture thereof, and wherein the antibody comprises:

(i) a heavy chain variable region (VH) comprising: (a) a VH complementarity determining region one (CDR-H1) comprising the amino acid sequence of SEQ ID NO: 13; (b) a VH complementarity determining region two (CDR-H2) comprising the amino acid sequence of SEQ ID NO: 14; and (c) a VH complementarity determining region three (CDR-H3) comprising the amino acid sequence of SEQ ID NO: 15, and (ii) a light chain variable region (VL) comprising: (a) a VL complementarity determining region one (CDR-L1) comprising the amino acid sequence of SEQ ID NO: 8; (b) a VL complementarity determining region two (CDR-L2) comprising the amino acid sequence of SEQ ID NO: 9; and (c) a VL complementarity determining region three (CDR-L3) comprising the amino acid sequence of SEQ ID NO: 10.

2. The stable pharmaceutical formulation of claim 1, wherein the antibody comprises a VH comprising the amino acid sequence of SEQ ID NO: 18, and a VL comprising the amino acid sequence of SEQ ID NO: 11.

3. The stable pharmaceutical formulation of claim 1, wherein the antibody comprises a VH sequence encoded by the insert present in the plasmid deposited under ATCC Accession No. PTA-122329, and a VL sequence encoded by the insert present in the plasmid deposited under ATCC Accession No. PTA-122328.

4. The stable pharmaceutical formulation of claim 1, wherein the antibody comprises a heavy chain comprising the amino acid sequence of SEQ ID NO: 19, and a light chain comprising the amino acid sequence of SEQ ID NO: 12.

5. The stable pharmaceutical formulation of claim 1, wherein the concentration of the antibody is about 100 mg/mL, about 115 mg/mL or about 150 mg/mL.

6. A stable pharmaceutical formulation consisting of: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, and 0.05 mg/mL disodium edetate dihydrate, wherein the histidine buffer comprises L-histidine, L-histidine monohydrochloride or a mixture thereof, wherein the antibody comprises a heavy chain variable region comprising the amino acid sequence of SEQ ID NO: 18, and a light chain variable region comprising the amino acid sequence of SEQ ID NO: 11, and wherein the formulation has a pH of 5.8.

7. A stable pharmaceutical formulation consisting of: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, and 0.05 mg/mL disodium edetate dihydrate, wherein the histidine buffer comprises L-histidine, L-histidine monohydrochloride or a mixture thereof, wherein the antibody comprises a heavy chain comprising the amino acid sequence of SEQ ID NO: 19, and a light chain comprising the amino acid sequence of SEQ ID NO: 12, and wherein the formulation has a pH of 5.8.

8. A stable pharmaceutical formulation consisting of: 150 mg/mL of an antibody that specifically binds to an epitope in Kunitz Domain 2 (K2) of Tissue Factor Pathway Inhibitor (TFPI), 20 mM histidine buffer, 85 mg/mL sucrose, 0.2 mg/mL polysorbate 80, and 0.05 mg/mL disodium edetate dihydrate, wherein the histidine buffer comprises L-histidine, L-histidine monohydrochloride or a mixture thereof, wherein the antibody comprises a heavy chain comprising the amino acid sequence of SEQ ID NO: 17, and a light chain comprising the amino acid sequence of SEQ ID NO: 12, and wherein the formulation has a pH of 5.8.

9. The stable pharmaceutical formulation of claim 1, wherein the formulation has a shelf life of at least about 24 months at 5±3° C.

10. The stable pharmaceutical formulation of claim 1, wherein the formulation has less than about 7% high molecular mass species (HMMS) at 40° C./75% relative humidity (RH) for up to 1 month, 2 months, 3 months, 4 months, 5 months, or 6 months, optionally as measured by size exclusion high performance liquid chromatography (SE-HPLC).

11. The stable pharmaceutical formulation of claim 1, wherein the formulation has less than about 3% HMMS at 40° C. for up to 1 month, 2 months, or 3 months, optionally as measured by SE-HPLC.

12. The stable pharmaceutical formulation of claim 1, wherein the formulation has less than about 2% HMMS at 40° C. for up to 1 month, optionally as measured by SE-HPLC.

13. A method of shortening bleeding time, comprising administering to a subject in need thereof a therapeutically effective amount of the stable pharmaceutical formulation of claim 1.

14. A method of treating a deficiency in blood coagulation or a bleeding disorder, comprising administering to a subject in need thereof a therapeutically effective amount of the stable pharmaceutical formulation of claim 1.

15. A method of treating hemophilia A, B or C, comprising administering to a subject in need thereof a therapeutically effective amount of the stable pharmaceutical formulation of claim 1.

16. A method of treating von Willebrand Disease (vWD), comprising administering to a subject in need thereof a therapeutically effective amount of the stable pharmaceutical formulation of claim 1.

17. A method for reducing the activity of TFPI, comprising administering to a subject in need thereof a therapeutically effective amount of the stable pharmaceutical formulation of claim 1.

18. The method of claim 13, wherein the stable pharmaceutical formulation is administered to the subject subcutaneously or intravenously.

* * * * *

SEQUENCE LISTING

<160> NUMBER OF SEQ ID NOS: 25

<210> SEQ ID NO 1
<211> LENGTH: 149
<212> TYPE: PRT
<213> ORGANISM: Artificial Sequence
<220> FEATURE:
<223> OTHER INFORMATION: Synthetic Construct

<400> SEQUENCE: 1

```
Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp
145
```

<210> SEQ ID NO 2
<211> LENGTH: 254
<212> TYPE: PRT
<213> ORGANISM: Artificial Sequence
<220> FEATURE:
<223> OTHER INFORMATION: Synthetic Construct

<400> SEQUENCE: 2

```
Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140
```

-continued

```
Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys
                245                 250


<210> SEQ ID NO 3
<211> LENGTH: 189
<212> TYPE: PRT
<213> ORGANISM: Artificial Sequence
<220> FEATURE:
<223> OTHER INFORMATION: Synthetic Construct

<400> SEQUENCE: 3

Asp Ala Ala Gln Glu Pro Thr Gly Asn Asn Ala Glu Ile Cys Leu Leu
1               5                   10                  15

Pro Leu Asp Tyr Gly Pro Cys Arg Ala Leu Leu Leu Arg Tyr Tyr Tyr
            20                  25                  30

Asp Arg Tyr Thr Gln Ser Cys Arg Gln Phe Leu Tyr Gly Gly Cys Glu
        35                  40                  45

Gly Asn Ala Asn Asn Phe Tyr Thr Trp Glu Ala Cys Asp Asp Ala Cys
    50                  55                  60

Trp Arg Ile Glu Lys Val Pro Lys Val Cys Arg Leu Gln Val Ser Val
65                  70                  75                  80

Asp Asp Gln Cys Glu Gly Ser Thr Glu Lys Tyr Phe Phe Asn Leu Ser
                85                  90                  95

Ser Met Thr Cys Glu Lys Phe Phe Ser Gly Gly Cys His Arg Asn Arg
            100                 105                 110

Ile Glu Asn Arg Phe Pro Asp Glu Ala Thr Cys Met Gly Phe Cys Ala
        115                 120                 125

Pro Lys Lys Ile Pro Ser Phe Cys Tyr Ser Pro Lys Asp Glu Gly Leu
    130                 135                 140

Cys Ser Ala Asn Val Thr Arg Tyr Tyr Phe Asn Pro Arg Tyr Arg Thr
145                 150                 155                 160

Cys Asp Ala Phe Thr Tyr Thr Gly Cys Gly Gly Asn Asp Asn Asn Phe
                165                 170                 175

Val Ser Arg Glu Asp Cys Lys Arg Ala Cys Ala Lys Ala
            180                 185


<210> SEQ ID NO 4
<211> LENGTH: 146
<212> TYPE: PRT
<213> ORGANISM: Artificial Sequence
<220> FEATURE:
<223> OTHER INFORMATION: Synthetic Construct

<400> SEQUENCE: 4

Leu Ser Glu Glu Ala Asp Asp Thr Asp Ser Glu Leu Gly Ser Met Lys
1               5                   10                  15
```

```
Pro Leu His Thr Phe Cys Ala Met Lys Ala Asp Asp Gly Pro Cys Lys
            20                  25                  30

Ala Met Ile Arg Ser Tyr Phe Phe Asn Met Tyr Thr His Gln Cys Glu
        35                  40                  45

Glu Phe Ile Tyr Gly Gly Cys Glu Gly Asn Glu Asn Arg Phe Asp Thr
    50                  55                  60

Leu Glu Glu Cys Lys Lys Thr Cys Ile Pro Gly Tyr Glu Lys Thr Ala
65                  70                  75                  80

Val Lys Ala Ala Ser Gly Ala Glu Arg Pro Asp Phe Cys Phe Leu Glu
                85                  90                  95

Glu Asp Pro Gly Leu Cys Arg Gly Tyr Met Lys Arg Tyr Leu Tyr Asn
            100                 105                 110

Asn Gln Thr Lys Gln Cys Glu Arg Phe Val Tyr Gly Gly Cys Leu Gly
        115                 120                 125

Asn Arg Asn Asn Phe Glu Thr Leu Asp Glu Cys Lys Lys Ile Cys Glu
    130                 135                 140

Asn Pro
145


<210> SEQ ID NO 5
<211> LENGTH: 149
<212> TYPE: PRT
<213> ORGANISM: Artificial Sequence
<220> FEATURE:
<223> OTHER INFORMATION: Synthetic Construct

<400> SEQUENCE: 5

Asp Ser Glu Glu Asp Glu Glu Tyr Thr Ile Ile Thr Asp Thr Glu Leu
1               5                   10                  15

Pro Pro Leu Lys Leu Met His Ser Phe Cys Ala Phe Lys Pro Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Gly Gly Asn Gln Asn
    50                  55                  60

Arg Phe Glu Ser Met Glu Glu Cys Lys Lys Val Cys Thr Arg Asp Asn
65                  70                  75                  80

Val Asn Arg Ile Ile Gln Thr Ala Leu Gln Lys Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Ser Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Thr Cys Glu Asp
145


<210> SEQ ID NO 6
<211> LENGTH: 149
<212> TYPE: PRT
<213> ORGANISM: Artificial Sequence
<220> FEATURE:
<223> OTHER INFORMATION: Synthetic Construct

<400> SEQUENCE: 6

Ala Ala Glu Glu Asp Glu Glu Phe Thr Asn Ile Thr Asp Ile Lys Pro
```

-continued

```
1               5                   10                  15

Pro Leu Gln Lys Pro Thr His Ser Phe Cys Ala Met Lys Val Asp Asp
            20                  25                  30

Gly Pro Cys Arg Ala Tyr Ile Lys Arg Phe Phe Phe Asn Ile Leu Thr
        35                  40                  45

His Gln Cys Glu Glu Phe Ile Tyr Gly Gly Cys Glu Gly Asn Glu Asn
    50                  55                  60

Arg Phe Glu Ser Leu Glu Glu Cys Lys Glu Lys Cys Ala Arg Asp Tyr
65                  70                  75                  80

Pro Lys Met Thr Thr Lys Leu Thr Phe Gln Lys Gly Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Ser Lys Gln Cys Glu Arg Phe Lys Tyr Gly
        115                 120                 125

Gly Cys Leu Gly Asn Leu Asn Asn Phe Glu Ser Leu Glu Glu Cys Lys
    130                 135                 140

Asn Thr Cys Glu Asn
145


<210> SEQ ID NO 7
<211> LENGTH: 148
<212> TYPE: PRT
<213> ORGANISM: Artificial Sequence
<220> FEATURE:
<223> OTHER INFORMATION: Synthetic Construct

<400> SEQUENCE: 7

Leu Pro Glu Glu Asp Asp Asp Thr Ile Asn Thr Asp Ser Glu Leu Arg
1               5                   10                  15

Pro Met Lys Pro Leu His Thr Phe Cys Ala Met Lys Ala Glu Asp Gly
            20                  25                  30

Pro Cys Lys Ala Met Ile Arg Ser Tyr Tyr Phe Asn Met Asn Ser His
        35                  40                  45

Gln Cys Glu Glu Phe Ile Tyr Gly Gly Cys Arg Gly Asn Lys Asn Arg
    50                  55                  60

Phe Asp Thr Leu Glu Glu Cys Arg Lys Thr Cys Ile Pro Gly Tyr Lys
65                  70                  75                  80

Lys Thr Thr Ile Lys Thr Thr Ser Gly Ala Glu Lys Pro Asp Phe Cys
                85                  90                  95

Phe Leu Glu Glu Asp Pro Gly Ile Cys Arg Gly Phe Met Thr Arg Tyr
            100                 105                 110

Phe Tyr Asn Asn Gln Ser Lys Gln Cys Glu Gln Phe Lys Tyr Gly Gly
        115                 120                 125

Cys Leu Gly Asn Ser Asn Asn Phe Glu Thr Leu Glu Glu Cys Arg Asn
    130                 135                 140

Thr Cys Glu Asp
145


<210> SEQ ID NO 8
<211> LENGTH: 14
<212> TYPE: PRT
<213> ORGANISM: Artificial Sequence
<220> FEATURE:
<223> OTHER INFORMATION: Synthetic Construct

<400> SEQUENCE: 8
```

```
Thr Gly Ser Ser Ser Asn Ile Gly Ala Gly Tyr Asp Val His
1               5                   10


<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Gly Asn Ser Asn Arg Pro Ser
1               5


<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Gln Ser Tyr Asp Ser Ser Leu Ser Gly Ser Gly Val
1               5                   10


<210> SEQ ID NO 11
<211> LENGTH: 113
<212> TYPE: PRT
<213> ORGANISM: Artificial Sequence
<220> FEATURE:
<223> OTHER INFORMATION: Synthetic Construct

<400> SEQUENCE: 11

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Phe Gly Gly Gly Thr Lys Leu Thr Val Leu
            100                 105                 110

Gly


<210> SEQ ID NO 12
<211> LENGTH: 218
<212> TYPE: PRT
<213> ORGANISM: Artificial Sequence
<220> FEATURE:
<223> OTHER INFORMATION: Synthetic Construct

<400> SEQUENCE: 12

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
```

```
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215


<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Gly Phe Thr Phe Ser Ser Tyr Ala Met Ser
1               5                   10


<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Ala Ile Ser Gly Ser Gly Gly Ser Thr Tyr Tyr Ala Asp Ser Val Lys
1               5                   10                  15

Gly


<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Leu Gly Ala Thr Ser Leu Ser Ala Phe Asp Ile
1               5                   10


<210> SEQ ID NO 16
<211> LENGTH: 120
```

-continued

<212> TYPE: PRT
<213> ORGANISM: Artificial Sequence
<220> FEATURE:
<223> OTHER INFORMATION: Synthetic Construct

<400> SEQUENCE: 16

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser
        115                 120
```

<210> SEQ ID NO 17
<211> LENGTH: 449
<212> TYPE: PRT
<213> ORGANISM: Artificial Sequence
<220> FEATURE:
<223> OTHER INFORMATION: Synthetic Construct

<400> SEQUENCE: 17

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 18
<211> LENGTH: 120
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110
```

-continued

```
Gly Thr Met Val Thr Val Ser Ser
        115                 120


<210> SEQ ID NO 19
<211> LENGTH: 449
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 20
<211> LENGTH: 120
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Ala Thr Ser Leu Ser Ala Phe Asp Ile Trp Gly Gln
            100                 105                 110

Gly Thr Met Val Thr Val Ser Ser
        115                 120


<210> SEQ ID NO 21
<211> LENGTH: 449
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Lys Leu Gly Ala Thr Ser Leu Ser Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 22
<211> LENGTH: 212
<212> TYPE: PRT
<213> ORGANISM: Artificial Sequence
<220> FEATURE:
<223> OTHER INFORMATION: Synthetic Construct
```

<400> SEQUENCE: 22

Asp Ile Glu Leu Thr Gln Pro Pro Ser Val Ser Val Ala Pro Gly Gln
1 5 10 15

Thr Ala Arg Ile Ser Cys Ser Gly Asp Asn Leu Arg Asn Tyr Tyr Ala
20 25 30

His Trp Tyr Gln Gln Lys Pro Gly Gln Ala Pro Val Val Val Ile Phe
35 40 45

Tyr Asp Val Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Trp Asp Gly Val Pro Val
85 90 95

Phe Gly Gly Gly Thr Lys Leu Thr Val Leu Gly Gln Pro Lys Ala Ala
100 105 110

Pro Ser Val Thr Leu Phe Pro Pro Ser Ser Glu Glu Leu Gln Ala Asn
115 120 125

Lys Ala Thr Leu Val Cys Leu Ile Ser Asp Phe Tyr Pro Gly Ala Val
130 135 140

Thr Val Ala Trp Lys Ala Asp Ser Ser Pro Val Lys Ala Gly Val Glu
145 150 155 160

Thr Thr Thr Pro Ser Lys Gln Ser Asn Asn Lys Tyr Ala Ala Ser Ser
165 170 175

Tyr Leu Ser Leu Thr Pro Glu Gln Trp Lys Ser His Arg Ser Tyr Ser
180 185 190

Cys Gln Val Thr His Glu Gly Ser Thr Val Glu Lys Thr Val Ala Pro
195 200 205

Thr Glu Cys Ser
210

<210> SEQ ID NO 23
<211> LENGTH: 446
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser Tyr
20 25 30

Gly Met Asp Trp Val Arg Gln Ala Pro Gly Lys Gly Leu Glu Trp Val
35 40 45

Ser Ser Ile Arg Gly Ser Arg Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Tyr Arg Tyr Trp Phe Asp Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys

```
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 24
<211> LENGTH: 219
<212> TYPE: PRT
<213> ORGANISM: Artificial Sequence
<220> FEATURE:
<223> OTHER INFORMATION: Synthetic Construct

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
```

-continued 50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Leu Gln Ala
85 90 95

Thr His Phe Pro Gln Thr Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 25
<211> LENGTH: 448
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Thr Pro Glu Lys Arg Leu Glu Trp Val
35 40 45

Ala Thr Ile Ser Arg Ser Gly Ser Tyr Ser Tyr Phe Pro Asp Ser Val
50 55 60

Gln Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Leu Gly Gly Tyr Asp Glu Gly Asp Ala Met Asp Ser Trp Gly
100 105 110

Gln Gly Thr Thr Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Lys Thr Tyr Thr Cys Asn Val Asp His

-continued

```
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```